(12) United States Patent
Ma et al.

(10) Patent No.: US 11,950,594 B2
(45) Date of Patent: Apr. 9, 2024

(54) METHODS AND COMPOSITIONS FOR INHIBITING FORMATION OF BIOFILMS

(71) Applicant: INSTITUTE OF MICROBIOLOGY, CHINESE ACADEMY OF SCIENCES, Beijing (CN)

(72) Inventors: Luyan Ma, Beijing (CN); Qing Wei, Beijing (CN); Pramod Bhasme, Beijing (CN); Di Wang, Beijing (CN)

(73) Assignee: INSTITUTE OF MICROBIOLOGY, CHINESE ACADEMY OF SCIENCES, Beijing (CN)

(*) Notice: Subject to any disclaimer, the term of this patent is extended or adjusted under 35 U.S.C. 154(b) by 135 days.

(21) Appl. No.: 17/454,626

(22) Filed: Nov. 12, 2021

(65) Prior Publication Data

US 2022/0167614 A1 Jun. 2, 2022

Related U.S. Application Data

(63) Continuation of application No. PCT/CN2019/086921, filed on May 14, 2019.

(51) Int. Cl.
*A01N 35/06* (2006.01)

(52) U.S. Cl.
CPC .................... *A01N 35/06* (2013.01)

(58) Field of Classification Search
CPC ...................................... A01N 35/06
See application file for complete search history.

(56) References Cited

U.S. PATENT DOCUMENTS

| | | | |
|---|---|---|---|
| 7,427,408 | B2 | 9/2008 | Merritt et al. |
| 8,507,554 | B2 | 8/2013 | Yoon et al. |
| 9,409,955 | B2 | 8/2016 | Reguera et al. |
| 2018/0042243 | A1 | 2/2018 | Ma et al. |
| 2018/0371029 | A1 | 12/2018 | Lovley et al. |

FOREIGN PATENT DOCUMENTS

WO 2012017454 A1 2/2012

OTHER PUBLICATIONS

Notes Konidala et al (Asian J Pharm Clin Res, vol. 13, Issue 5, 2020, 28-37). (Year: 2020).*

(Continued)

*Primary Examiner* — Benjamin J Packard
(74) *Attorney, Agent, or Firm* — METIS IP LLC

(57) ABSTRACT

The present disclosure discloses a method for inhibiting formation of a biofilm of bacteria. Specifically, the method may include treating the bacteria with an effective amount of a coumarin-chalcone compound. While inhibiting the formation of the biofilm of the bacteria, the effective amount of the coumarin-chalcone compound may reduce virulences of the bacteria and enhance a susceptibility of the bacteria to an antibiotic when applied in combination with the antibiotic. The present disclosure further discloses a composition including an effective amount of the coumarin-chalcone compound. The composition may be used to inhibit the formation of the biofilm of bacteria. The composition may also include an antibiotic, a minimal inhibitory concentration and a minimal biofilm eliminate concentration of which are reduced when the composition is used.

20 Claims, 17 Drawing Sheets

Specification includes a Sequence Listing.

(56) References Cited

OTHER PUBLICATIONS

J. C. Trivedi et al. / Tetrahedron Letters 48 (2007) 8472-8474. (Year: 2007).*
F. Jerry Reen et al., Coumarin: A Novel Player in Microbial Quorum Sensing and Biofilm Formation Inhibition, Applied Microbiology and Biotechnology, 102: 2063-2073, 2018.
Shahenda M. El-Messery et al., Synthesis, Antimicrobial, Antibiofilm Evaluation, and Molecular Modelling Study of New Chalcone Linked Amines Derivatives, Journal of Enzyme Inhibition and Medicinal Chemistry, 33(1): 818-832, 2018.
Dawn E. Holmes et al., The Electrically Conductive Pili of *Geobacter* Species are a Recently Evolved Feature for Extracellular Electron Transfer, Microbial Genomics, 1-20, 2016.
José A. Gutiérrez-Barranquero et al., Deciphering the Role of Coumarin as a Novel Quorum Sensing Inhibitor Suppressing Virulence Phenotypes in Bacterial Pathogens, Appl Microbiol Biotechnol, 2015, 14 pages.
International Search Report in PCT/CN2019/086921 dated Feb. 18, 2020, 10 pages.
Written Opinion in PCT/CN2019/086921 dated Feb. 18, 2020, 14 pages.
Kallappa M. Hosamani et al., Microwave-assisted Synthesis of New Fluorinated Coumarin-pyrimidine Hybrids as Potent Anticancer Agents, Their DNA Cleavage and X-ray Crystal Studies, RSC Advances., 2015, 11 pages.
Thrineshen Moodley et al., The Synthesis, Structural Elucidation and Antimicrobial Activity of 2- and 4-Substituted-Coumarinyl Chalcones, Magn. Reson. Chem., 2016, 8 pages.
Lívia Slobodníková et al., Antibiofilm Activity of Plant Polyphenols, Molecules, 2016, 15 pages.
First Office Action in Chinese Application No. 201980003736.5 dated Dec. 28, 2020, 13 pages.
Decision to Grant Patent Right for Invention in Chinese Application No. 201980003736.5 dated Jun. 23, 2021, 3 pages.

* cited by examiner

METHODS AND COMPOSITIONS FOR INHIBITING FORMATION OF BIOFILMS

CROSS-REFERENCE TO RELATED APPLICATIONS

This application is a continuation of International Application No. PCT/CN2019/086921, filed on May 14, 2019, the contents of which are hereby incorporated by reference.

TECHNICAL FIELD

The present disclosure relates to the field of biotechnology, and in particular, to methods and compositions for inhibiting the formation of biofilms.

BACKGROUND

Biofilm (or "bacteria biofilm") generally refers to communities of microorganisms encased by extracellular polymeric substances (EPS), and is prevalent in natural, industrial, and clinical settings. The biofilm may enhance the survival of the microorganisms, enabling them to adapt to diverse environments. For example, in the medical field, studies have indicated that about 65% of human bacterial infections are related to biofilms, and antibiotic resistance of the microorganisms in the biofilms is hundreds or even thousands of times higher than that in a plankton state. Biofilm bacteria have a strong resistance to antibiotics and the host immune system, giving rise to serious clinical problems and many chronic infectious that are notoriously difficult to eradicate.

One of the most important features of biofilms is self-secreted extracellular polymeric substances (EPS) consisting of mainly polysaccharides, proteins, and extracellular DNA (eDNA), which function as a matrix or glue, holding biofilm cells together and protecting cells from antibiotics and shear forces in fluid environments. By forming a matrix-encased multicellular aggregate, cells can also escape engulfment by phagocytic cells within a mammalian host. EPS not only promote microorganisms (e.g., bacteria) to attach all kinds of surfaces (e.g., a biomedical material or a mucosal surface of a biological organism), but also trap antibiotics or influence antibiotics to penetrate into the bacterial communities. Therefore, in some cases, most drugs can only kill microorganisms on the outer layer of the biofilm, yet microorganisms inside the biofilm can escape the killing effect of antibiotics to survive continuously, which is also the main reason for the generation of antibiotic-resistance mutation. Thus, the biofilms become a potential source of injections, which may cause refractory infections relating to clinical biofilms.

Another feature of the bacteria is to produce virulence factors having toxicity, for example, *Pseudomonas aeruginosa* (*P. aeruginosa*) is capable of producing a plurality of virulence factors such as pyoverdine, pyocyanin, HCN, and protease, etc., to invade infected host cells. The production of virulence factors is controlled by a precisely regulation system. The most virulence factors in *Pseudomonas aeruginosa* are activated by quorum sensing (QS) systems. There are at least three QS systems in *Pseudomonas aeruginosa*, such as LasR/LasI, RhlR/RhlI, and PQS systems. The three QS systems interact with each other and regulate the expression of different virulence factors to control bacterial virulence. In recent years, researchers have developed many chemical inhibitors targeting on these three QS systems to prevent infections caused by these pathogenic bacteria. However, there are still many problems, such as high cost, unsatisfactory effect, and unclear inhibition mechanism. Therefore, it is desired to develop preparations (e.g., compounds) and methods for effectively inhibiting biofilms formed by microorganisms.

SUMMARY

One aspect of some embodiments of the present disclosure provides a method for inhibiting formation of a biofilm of bacteria. The method may include treating the bacteria with an effective amount of a coumarin-chalcone compound. A molecular formula of the coumarin-chalcone compound may be as follows:

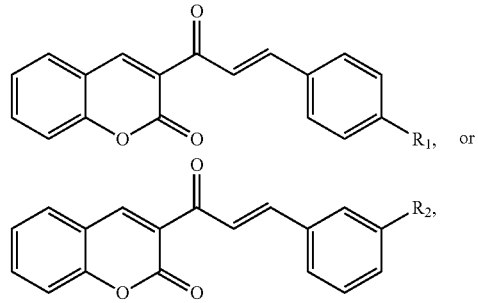

wherein $R_1$ may be selected from —H, —$CH_3$, —$OCH_3$, —Cl, —Br, —F, —OH, —$NO_2$; and $R_2$ may be selected from —$OCH_3$, —Cl, —Br, —$NO_2$.

In some embodiments, the coumarin-chalcone compound may inhibit the formation of the biofilm by reducing production of Psl polysaccharide in the bacteria at a transcription level.

In some embodiments, the coumarin-chalcone compound may inhibit the formation of the biofilm by reducing a level of c-di-GMP in the bacteria, and the c-di-GMP may be able to promote conversion of plankton into the biofilm.

In some embodiments, the coumarin-chalcone compound may inhibit the formation of the biofilm by reducing quorum sensing, virulence factors regulated by the quorum sensing may be reduced by downregulating the expression of quorum sensing regulators in the bacteria, and the quorum sensing regulators may include at least one of LasR, RhlR, or PqsR.

In some embodiments, a concentration of the effective amount of the coumarin-chalcone compound may be about 5 mM.

In some embodiments, the effective amount of the coumarin-chalcone compound may inhibit the formation of at least 30% of the biofilm when other conditions are the same.

In some embodiments, the effective amount of the coumarin-chalcone compound may further reduce the virulence of the bacteria.

In some embodiments, the bacteria may include Gram negative bacteria.

In some embodiments, the Gram negative bacteria may include *Pseudomonas aeruginosa* or *Escherichia coli*.

In some embodiments, the bacteria may include Gram positive bacteria.

In some embodiments, the Gram positive bacteria may include *Staphylococcus aureus*.

In some embodiments, the effective amount of the coumarin-chalcone compound may inhibit the formation of at least 50% of the biofilm when other conditions are the same.

In some embodiments, the effective amount of the coumarin-chalcone compound may inhibit the formation of at least 60% of the biofilm when other conditions are the same.

In some embodiments, the bacteria are *Staphylococcus aureus*, and the effective amount of the coumarin-chalcone compound may inhibit the formation of at least 30% of *Staphylococcus aureus* biofilm when other conditions are the same.

In some embodiments, the bacteria are *Escherichia coli*, and the effective amount of the coumarin-chalcone compound may inhibit the formation of at least 60% of *Escherichia coli* biofilm when other conditions are the same.

In some embodiments, the bacteria are *Pseudomonas aeruginosa*, and the effective amount of the coumarin-chalcone may inhibit the formation of at least 70% of *Pseudomonas aeruginosa* biofilm when other conditions are the same.

In some embodiments, the molecular formula of the coumarin-chalcone compound may be as follows:

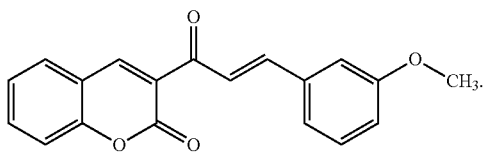 [SMILES: COc1cccc(/C=C/C(=O)c2cc3ccccc3oc2=O)c1]

Another aspect of some embodiments of the present disclosure provides a composition for inhibiting formation of a biofilm. The composition may include an effective amount of a coumarin-chalcone compound. A molecular formula of the coumarin-chalcone compound may be as follows:

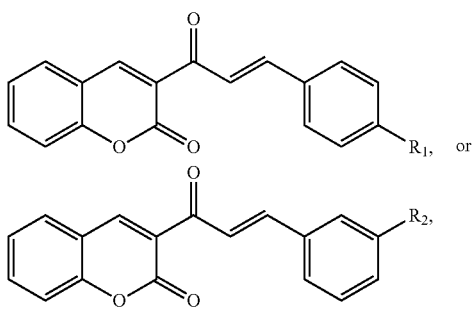

wherein $R_1$ may be selected from —H, —$CH_3$, —$OCH_3$, —Cl, —Br, —F, —OH, —$NO_2$; and $R_2$ may be selected from —$OCH_3$, —Cl, —Br, —$NO_2$.

In some embodiments, the composition may be configured to reduce production of Psl polysaccharide at a transcription level.

In some embodiments, the composition may be configured to inhibit the formation of the biofilm by reducing a level of c-di-GMP in bacteria, and the c-di-GMP may be able to promote conversion of plankton into the biofilm.

In some embodiments, the composition may be configured to inhibit the formation of the biofilm by reducing quorum sensing, virulence factors regulated by the quorum sensing may be reduced by downregulating the expression of quorum sensing regulators in the bacteria, and the quorum sensing regulators may include at least one of LasR, RhlR, or PqsR.

In some embodiments, a concentration of the effective amount of the coumarin-chalcone compound is about 5 mM.

In some embodiments, the effective amount of coumarin-chalcone compound may inhibit at least 30% of the biofilm when other conditions are the same.

In some embodiments, the composition may be further configured to reduce the virulence of the bacteria.

In some embodiments, the bacteria may include Gram negative bacteria.

In some embodiments, the Gram negative bacteria may include *Pseudomonas aeruginosa* or *Escherichia coli*.

In some embodiments, the bacteria may include Gram positive bacteria.

In some embodiments, the Gram positive bacteria may include *Staphylococcus aureus*.

In some embodiments, the bacteria are *Staphylococcus aureus*, and the effective amount of coumarin-chalone compound may inhibit the formation of at least 30% of *Staphylococcus aureus* biofilm when other conditions are the same.

In some embodiments, the bacteria are *Escherichia coli*, and the effective amount of coumarin-chalcone compound may inhibit the formation of at least 60% of *Escherichia coli* biofilm when other conditions are the same.

In some embodiments, the bacteria are *Pseudomonas aeruginosa*, and the effective amount of the coumarin-chalcone compound may inhibit the formation of at least 70% of *Pseudomonas aeruginosa* biofilm when other conditions are the same.

In some embodiments, the composition may further include an antibiotic including at least one of amoxicillin, doxycycline, tetracycline, minocycline, cephalexin, cefuroxime, ciprofloxacin, moxifloxacin, clindamycin, lincomycin, clarithromycin, azithromycin, sulfapyridine, sulfamoxole, dalbavancin, telavancin, gentamicin, tobramycin, meropenem, doripenem, metronidazole, azithromycin, or levofloxacin.

In some embodiments, the composition may be further configured to enhance a sensitivity of the bacteria to the antibiotic.

In some embodiments, the composition may be further configured to reduce a minimal inhibitory concentration of the antibiotic and a minimal biofilm eliminate concentration of the antibiotic.

In some embodiments, a concentration of the effective amount of the coumarin-chalcone compound may be about 5 mM.

In some embodiments, the molecular formula of the coumarin-chalcone compound may be as follows:

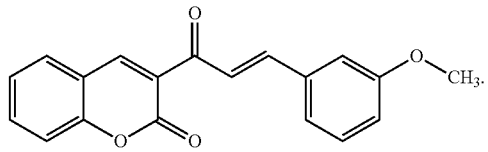 [SMILES: COc1cccc(/C=C/C(=O)c2cc3ccccc3oc2=O)c1]

BRIEF DESCRIPTION OF THE DRAWINGS

The present disclosure is further illustrated in terms of exemplary embodiments. These exemplary embodiments are described in detail with reference to the drawings. These embodiments are not limited, in these embodiments, the same number denotes the same structure, wherein.

DETAILED DESCRIPTION

Figure 1:
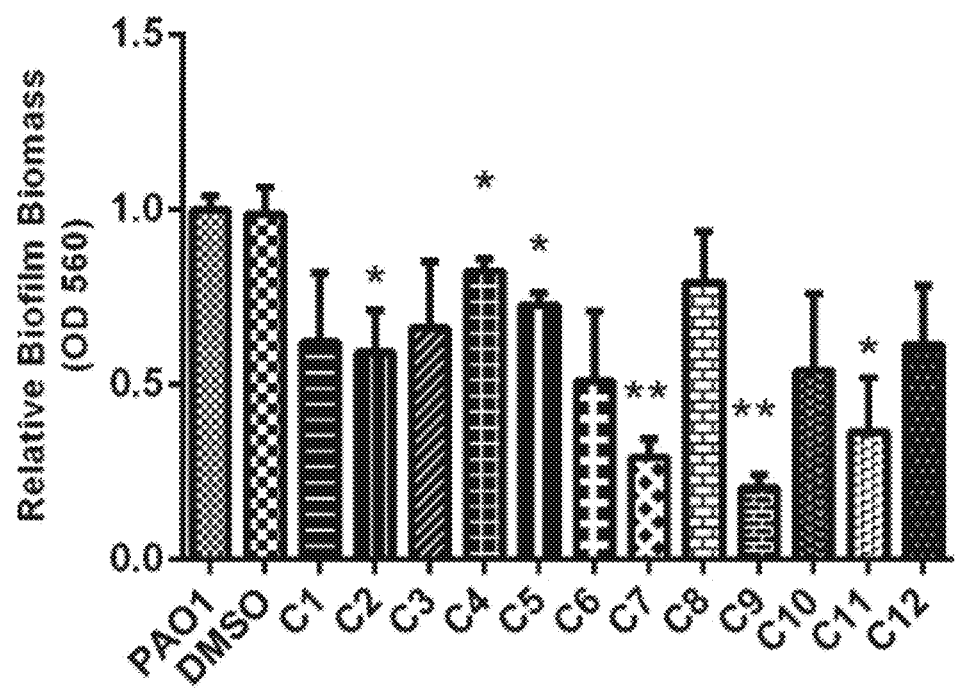
FIG. 1 is a schematic diagram illustrating inhibitory effects of coumarin-chalcone compounds C1 to C12 to bacteria biofilms.

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those ordinary skilled in the art, without further creative efforts, may apply the present disclosure to other similar scenarios according to these drawings. Unless obviously obtained from the context or the context illustrates otherwise, the same numeral in the drawings refers to the same structure or operation.

As used in the disclosure and the appended claims, the singular forms "a," "an," and "the" include plural referents unless the content clearly dictates otherwise. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

The "CdrA protein", "protein CdrA", "extracellular protein CdrA", and "CdrA" described in the present disclosure may be used interchangeably, which refer to the extracellular protein synthesized by *Pseudomonas aeruginosa* (*P. aeruginosa*) or the homologous protein synthesized by other similar microorganisms. It should be understood that the terms "CdrA protein", "protein CdrA", "extracellular protein CdrA", and "CdrA" may also include a wild-type and mutant types of CdrA protein. CdrA protein may include a full-length CdrA protein, a mature CdrA protein, an active fragment of the CdrA protein, and/or a derived protein of the CdrA protein.

The terms "Psl," "Psl polysaccharide," and "extracellular polysaccharide Psl" in the present disclosure may be used interchangeably, which refer to an exopolysaccharide synthesized by a polysaccharide synthesis site of *Pseudomonas aeruginosa* or other similar microorganisms. The terms "culture medium" and "plate" in the present disclosure may be used interchangeably, which refer to a nutrient matrix composed of different nutrients that can be provided for the growth and reproduction of microorganisms.

An aspect of the present disclosure provides a method for inhibiting formation of a biofilm. The method may include treating bacteria with an effective amount of a coumarin-chalcone compound (e.g., C1-C12). The molecular formula of the coumarin-chalcone compound may be as follows:

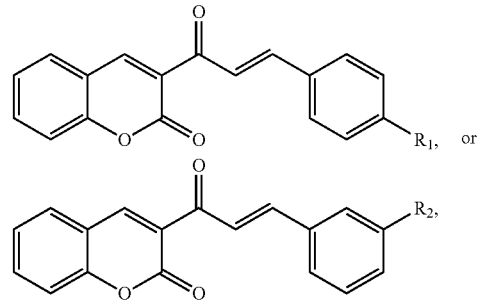

where $R_1$ may be selected from —H, —$CH_3$, —$OCH_3$, —Cl, —Br, —F, —OH, —$NO_2$; and $R_2$ may be selected from —$OCH_3$, —Cl, —Br, —$NO_2$. As can be seen from the above molecular formula, the disclosed coumarin-chalcone compounds (also be referred to as coumarin-chalcone derivatives) have highly similar skeleton structures.

Biofilm, also known as bacterial aggregate, is a microbial aggregate. Microbial cells in the microbial aggregate may be bonded to each other on a surface of a subject and embedded in the extracellular polymer (EPS) matrix secreted by themselves. In some embodiments, microorganisms that easily form biofilms may be bacteria, such as *P. aeruginosa, Pseudomonas stutzeri* (*P. stutzeri*), *Acinetobacter baumannii* (*A. baumannii*), *Staphylococcus aureus* (*S. aureus*), *Streptococcus pneumoniae* (*S. pneumoniae*), *Paenibacillus polymyxa* (*P. polymyxa*), *Sinorhizobium meliloti* (*S. meliloti*), *Bacillus amyloliquefaciens* (*B. amyloliquefaciens*), etc. The subject whose surface is likely to allow microorganisms to form a biofilm may include metals, glass, plastics, rocks, textiles, wool, sponges, human/animal organs or tissues (e.g., lungs, ears, skin, etc.), or the like, or any combination thereof.

Extracellular polysaccharide is an important extracellular polymer. In some embodiments, the extracellular polysaccharide may be an important component of the biofilm which helps in maintaining biofilm architecture. In some embodiments, the extracellular polysaccharide may be a linear long-chain molecule. In some embodiments, the extracellular polysaccharide may also be a branched long-chain molecule. In some embodiments, the extracellular polysaccharide may cause stratification between colonies and establish pathways for the transportation of nutrients and metabolic waste. In some embodiments, the extracellular polysaccharide may also provide protection for the biofilm from various external factors, such as desiccation, immune factors, phagocytes, amoebas, etc. In some embodiments, the formation of the biofilm may be related to a variety of extracellular polysaccharides. For example, the formation of *Pseudomonas aeruginosa* biofilm is related to three polysaccharides including Psl, Pel, and alginate.

In some embodiments, the Psl polysaccharide may be an important extracellular polysaccharide. The Psl polysaccharide may be composed of pentasaccharide repeating units formed by D-mannose, D-glucose, and L-rhamnose. The Psl polysaccharide may be produced by a series of proteins encoded by a gene cluster composed of 15 co-transcribed genes (pslA-pslO, PA2231~PA2245), of which the first 11 of the co-transcribed genes are necessary for the production of Psl polysaccharide. For example, *Pseudomonas aeruginosa* PA14 lost its ability to produce Psl polysaccharide due to the deletion of pslA-pslD genes.

In some embodiments, the Psl polysaccharide is an indispensable component for the formation of biofilm, which is essential for the adsorption of bacteria on a surface of a medium, maintaining the structure of the biofilm, and providing the interaction between cells and the surface of the medium. In some embodiments, the Psl polysaccharide may form a fibrous web, which allows bacterial populations to enter and cover the biofilm. In some embodiments, the Psl polysaccharide may enhance adhesion between bacterial cells and between bacterial cell and media. In some embodiments, the Psl polysaccharide may also change the morphology of the colony. In some embodiments, the Psl polysaccharide may have a signal function, which may increase a level of the second messenger molecule c-di-GMP between bacterial cells by stimulating two diguanylate SiaD and SadC, to form a unique positive feedback regulatory circuit and finally improve the yield of Psl polysaccharide. In some embodiments, the Psl polysaccharide may also impart antigenicity to bacteria and protect bacterial cells from the attack of host immune system. For example, the Psl polysaccharide may directly stimulate the activity of NF-κB by enhancing the contact between the bacterial cells and epithelial cells and promote flagellum mediated pro-inflammatory signals. As another example, the Psl polysaccharide of *Pseudomonas aeruginosa* may weaken the phagocytosis of neutrophils and reduce the occurrence of oxidative stress response by limiting complement-mediated conditioning. In some embodiments, the Psl polysaccharide may also play a role in the generation of antibiotic resistance in bacteria. For example, the Psl polysaccharide may promote the resistance of bacteria to biofilm inhibitor polysorbate 80. As another example, the micro-colony structure formed by the Psl polysaccharide in the biofilm makes *Pseudomonas aeruginosa* insensitive to the treatment of antibiotics.

In some embodiments, an effective amount of the coumarin-chalcone compound may reduce the production of the Psl polysaccharide, resulting in dispersion of the biofilm. In some embodiments, a composition containing an effective amount of the coumarin chalcone compound in a form of a solution, suspension, emulsion, or any combination thereof may be used to treat bacteria to inhibit, reduce, disperse, or destroy biofilms that have been formed or biofilms to be formed. In some embodiments, a composition containing an effective amount of the coumarin-chalcone compound in a solid form (e.g., cream, powder, particles, etc.) may be used to treat the bacteria. In some embodiments, the effective amount of the coumarin-chalcone compound may be a coumarin-chalcone compound C9, which may reduce the production of the Psl polysaccharide (see FIG. 4 and the descriptions thereof).

Cyclic diguanylate (c-di-GMP) may be a ubiquitous second messenger molecule in bacteria. In some embodiments, c-di-GMP may be involved in mediating a variety of physiological processes of the bacteria, such as flagella mediated movement, cell differentiation, cell morphology, transition from a motile lifestyle to a biofilm state, biofilm formation, production of virulence factors, or the like, or any combination thereof.

In some embodiments, genes and protein networks dominated by c-di-GMP in bacterial cells may be considered to be the key to the formation of biofilms. As the second messenger, C-di-GMP widely exists in microbial populations, such as *Pseudomonas aeruginosa, Caulobacter crescentus, Escherichia coli (E. coli), Acetobacter xylinum (A. xylinum)*, etc. A concentration of intracellular c-di-GMP in the bacteria may be in a wide range between 10 nM and 10 μM. In some embodiments, the effective amount of the coumarin-chalcone compound may reduce the production of c-di-GMP to achieve a purpose of inhibiting the formation of biofilms. In some embodiments, the effective amount of the coumarin-chalcone compound may be the coumarin-chalcone compound C9, which can reduce the production of c-di-GMP (see FIG. 7 and the descriptions thereof).

Quorum sensing (QS) refers to a population characteristic behavior caused by a change of physiological and biochemical characteristics due to an increase of population density during the growth of the microbial population that a few bacteria or a single bacteria does not possess. The population characteristic behavior may include bioluminescence, antibiotic synthesis, biofilm formation, secondary metabolite generation, toxic factor generation, etc. In some embodiments, the quorum sensing of microorganisms may include a plurality of quorum sensing systems. For example, *Pseudomonas aeruginosa* may mainly include three different levels of quorum sensing systems including las, rhl, and PQS. The corresponding three self-induced signal molecules are N-3-oxo-C12-HSL, C4-HSL, and quinolone, respectively. The binding of signal molecules to corresponding receptor proteins (e.g., transcription factors LasR, RhlR, and PqsR) may activate the transcription of a series of genes, such as LasI, RhlI, and PqsA.

In some embodiments, a quorum sensing process may be extremely closely related to the formation of the biofilm. For example, a mutant strain of *Pseudomonas aeruginosa* with lasI knocked out may only form a uniform thin biofilm, and its tolerance to various fungicides (e.g., hydrogen peroxide, tobramycin, etc.) may be greatly weakened. In some embodiments, the quorum sensing systems may help bacteria secrete extracellular polymers. For example, the las system of *Pseudomonas aeruginosa* may control the secretion of extracellular elastase and hydrolase. The rhl system may control the secretion of a biosurfactant (e.g., rhamnolipid). The PQS system may promote the secretion of *Pseudomonas aeruginosa* and lectin LecA. In some embodiments, the quorum sensing system may also regulate a surface movement ability of bacteria. In some embodiments, the effective amount of the coumarin-chalcone compound may downregulate an expression level of the QS gene. In some embodiments, the coumarin-chalcone compound may be the coumarin-chalcone compound C9.

Figure 12:
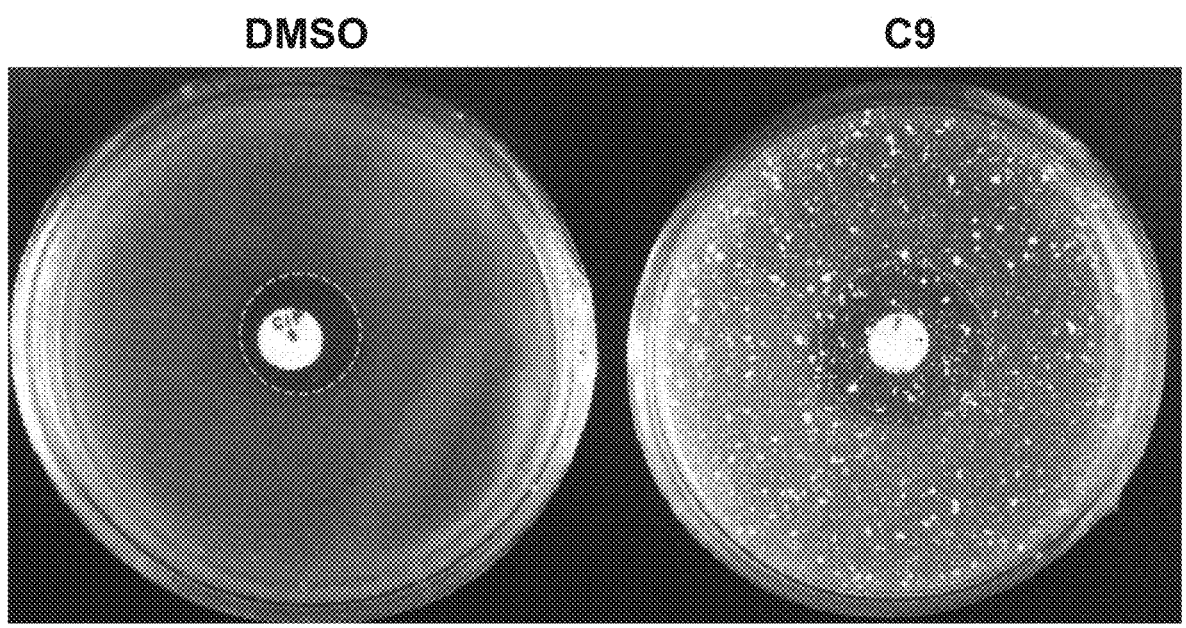
FIG. 12 is a schematic diagram illustrating an effect of a coumarin-chalcone compound C9 on enhancing a susceptibility of bacteria to an antibiotic drug.

In some embodiments, the effective amount of the coumarin-chalcone compound may be used to inhibit a biofilm formed by *Pseudomonas aeruginosa, Escherichia coli, Staphylococcus aureus*, or the like. FIG. 12 is a schematic diagram illustrating an effect of a coumarin-chalcone compound C9 on enhancing a susceptibility of bacteria to an antibiotic drug. As shown in FIG. 12 and the descriptions thereof, after treatment with the effective amount of the coumarin-chalcone compound C9, *Staphylococcus aureus* biofilm is reduced by 30% and *Escherichia coli* biofilm is reduced by 60%.

Another aspect of some embodiments of the present disclosure provides a composition for inhibiting formation of a biofilm. The composition may include a coumarin structure and a chalcone structure. The coumarin (2H-1-benzopyran-2-ketone) structure may have a connecting structure of benzene and α-pyranone ring, and actually contain an electron-rich π-π conjugated system with a high charge transport property. A coumarin derivative may be easy to interact with various enzymes and receptors in organisms through a weak bond interaction. In some embodiments, a coumarin derivative may have significant biological activities, such as an antibacterial activity, an antiviral activity, an anti-tuberculous activity, an anti-inflammatory activity, an anti-oxidant activity, an anti-cancer activity, or the like, or any combination thereof. Exemplary coumarin derivatives may include warfarin, armillarisin A, hymecromone, carbochrome, phenprocoumon, novobiocin, etc. Two aromatic rings of the chalcone (1,3-diaryl-2-propene-1-ketone) structure may be connected by a three-carbon system (i.e., α, β-unsaturated carbonyl). In some embodiments, a chalcone derivative may have significant biological activities, such as an antibacterial activity, an antiviral activity, an antifungal activity, an antimalarial activity, an anti-HIV activity, or the like, or any combination thereof. In some embodiments, the chalcone derivative may have a significant cytotoxic activity against various cancer cells. In some embodiments, the coumarin structure and the chalcone structure in a composition (e.g., C1-C12) may produce synergistic effects in biological activity.

Figure 4:
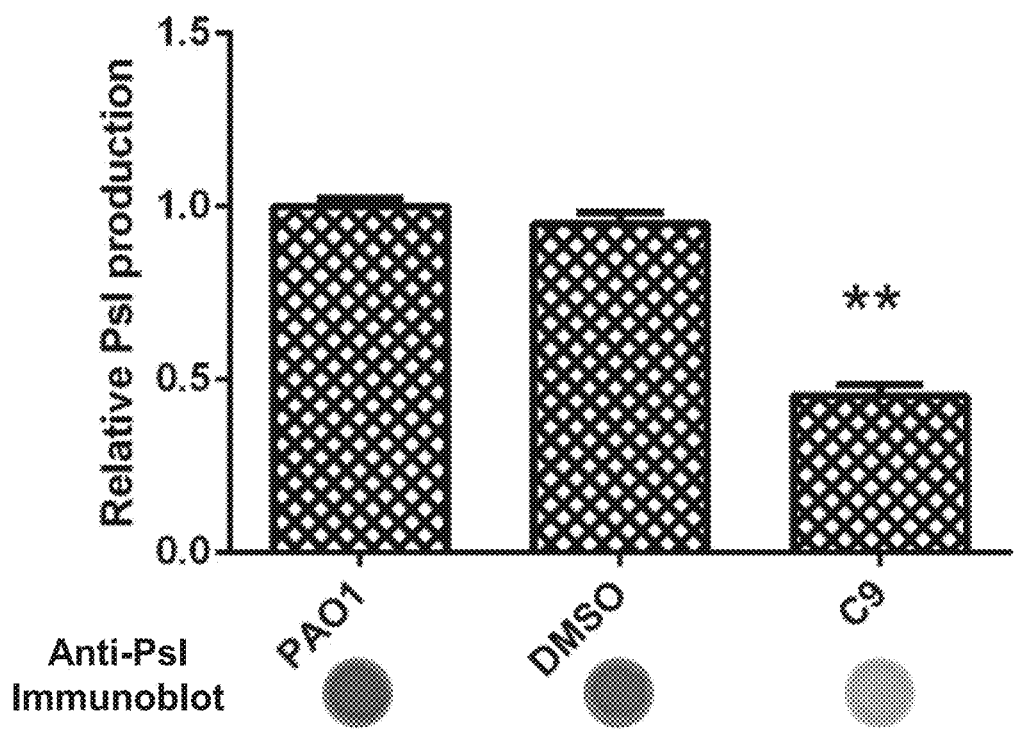
FIG. 4 is a schematic diagram illustrating Psl polysaccharide production of a blank group, a control group, and an experimental group treated with a coumarin-chalcone compound C9.
Figure 5:
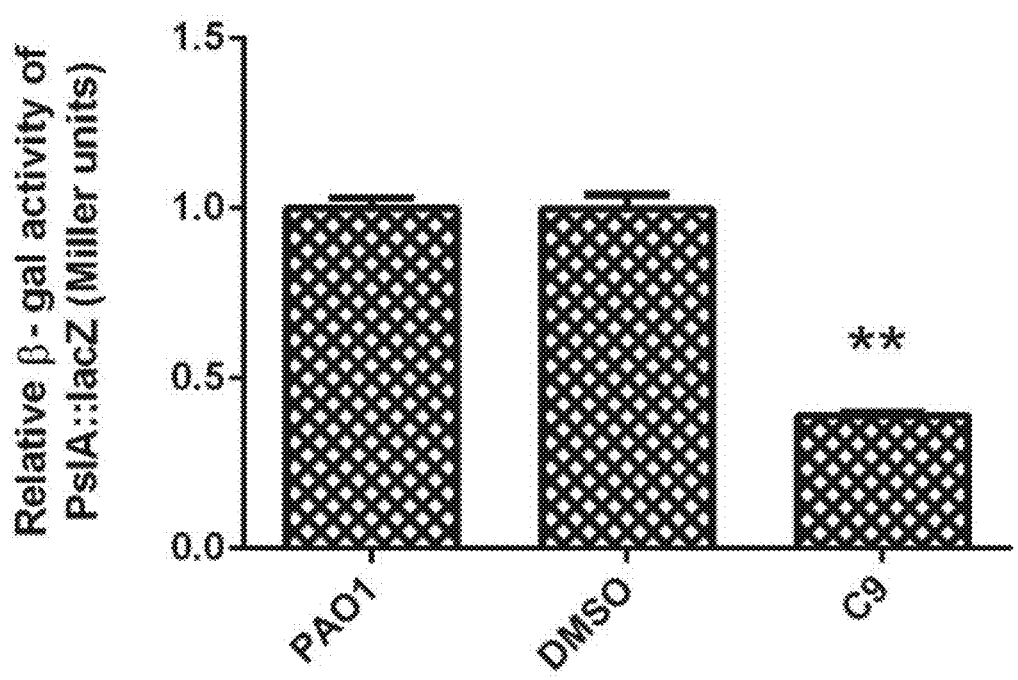
FIG. 5 is a schematic diagram illustrating transcription activities of pslA::lacZ of a blank group, a control group, and an experimental group treated with a coumarin-chalcone compound C9.
Figure 6:
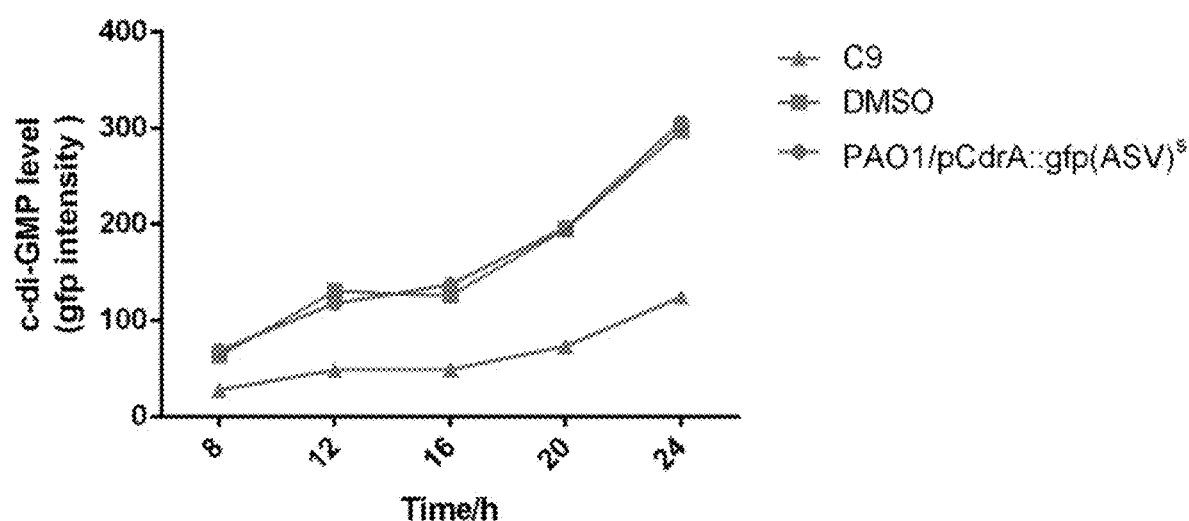
FIG. 6 is a schematic diagram illustrating levels of intracellular c-di-GMP of a blank group, a control group, and an experimental group treated with a coumarin-chalcone compound C9, wherein the c-di-GMP are indicated by the green fluorescent intensity of pCdrA::gfp$^s$.

In some embodiments, the composition may reduce the production of Psl and c-di-GMP by bacteria to inhibit the production of biofilm (see FIG. 4 to FIG. 6 and the descriptions thereof). In some embodiments, the coumarin-chalcone compound included in the composition may be the coumarin-chalcone compound C9.

In some embodiments, the coumarin structure may contain a methyl, an ethyl, an aldehyde, a methoxy, an ethoxy, a carboxyl, or the like, or any combination thereof. In some embodiments, the ability of the coumarin-chalcone compound for inhibiting the formation of biofilm or degrading the biofilm may be improved by modifying substituents of the coumarin structure and/or the chalcone structure. For example, the ability to combine with LasR may be enhanced.

In some embodiments, the composition may include the coumarin-chalcone compound, and a suitable carrier or auxiliary. The coumarin-chalcone compound may prevent or disperse the biofilm or bacterial aggregate. The carrier may be a solvent or solution (e. g., water, salt solution, etc.) that dissolves the coumarin-chalcone compound or other reagents. The auxiliary may include a buffer, a pH regulator, a reagent that can enhance the ability of the coumarin-chalcone compound to disperse the biofilm or bacterial aggregate, or the like, or any combination thereof.

In some embodiments, the composition may further include an antibiotic. As mentioned above, the biofilm may provide structural support and protection for bacteria embedded in it and contribute to the resistance of bacteria to antibiotics and/or adverse environments. In some embodiments, the coumarin-chalcone compound in the composition may destroy the biofilm and expose the bacteria. Once the biofilm is destroyed, the bacteria may lose the protection and structural support provided by the biofilm, thereby causing the bacteria more vulnerable or susceptibility to antibiotics. In some embodiments, destroying the biofilm may increase the susceptibility of bacteria to antibiotics. In some embodiments, the antibiotics may include amoxicillin, doxycycline, tetracycline, minocycline, cephalexin, cefuroxime, ciprofloxacin, moxifloxacin, clindamycin, lincomycin, clarithromycin, azithromycin, sulfapyridine, sulfamoxole, dalbavancin, telavancin, gentamicin, tobramycin, meropenem, doripenem, metronidazole, azithromycin, levofloxacin, or the like, or any combination thereof. In some embodiments, the coumarin-chalcone compound included in the composition may be the coumarin-chalcone compound C9.

In some embodiments, the composition may be a liquid, a solid, or a semi-solid. For example, the composition in liquid form may be a solution. The composition in solid form may be a sheet, powder, particles, nanoparticles, or the like. The composition in semi-solid form may be a suspensions, a cream, a paste, or the like.

In some embodiments, methods of dispersing the biofilm or bacterial aggregate may also include magnetic stirring, mechanical stirring, vortex oscillation, ultrasonic treatment, tissue homogenization, or the like, or any combination thereof. Treatment with coumarin-chalcone compound may be used in combination with one or more of the above methods.

In some embodiments, when the composition is used to inhibit, prevent, or disperse the biofilm or bacterial aggregate, an effective concentration of the coumarin-chalcone compound may be in a range of 0.1 μM to 100 mM. In some embodiments, the effective concentration of the coumarin-chalcone compound may be in a range of 0.1 mM to 100 mM. In some embodiments, the effective concentration of the coumarin-chalcone compound may be in a range of 1 mM to 100 mM. In some embodiments, the effective concentration of the coumarin-chalcone compound may be in a range of 1 mM to 90 mM. In some embodiments, the effective concentration of the coumarin-chalcone compound may be in a range of 1 mM to 80 mM. In some embodiments, the effective concentration of the coumarin-chalcone compound may be in a range of 1 mM to 70 mM. In some embodiments, the effective concentration of the coumarin-chalcone compound may be in a range of 1 mM to 60 mM. In some embodiments, the effective concentration of the coumarin-chalcone compound may be in a range of 1 mM to 50 mM. In some embodiments, the effective concentration of the coumarin-chalcone compound may be in a range of 1 mM to 40 mM. In some embodiments, the effective concentration of the coumarin-chalcone compound may be in a range of 1 mM to 30 mM. In some embodiments, the effective concentration of the coumarin-chalcone compound may be in a range of 1 mM to 20 mM. In some embodiments, the effective concentration of the coumarin-chalcone compound may be in a range of 1 mM-10 mM. In some embodiments, the effective concentration of the coumarin-chalcone compound may be in a range of 1 mM to 9 mM. In some embodiments, the effective concentration of the coumarin-chalcone compound may be in a range of 2 mM to 8 mM. In some embodiments, the effective concentration of the coumarin-chalcone compound may be in a range of 3 mM to 7 mM. In some embodiments, the effective concentration of the coumarin-chalcone compound may be in a range of 4 mM to 6 mM. In some embodiments, the effective concentration of the coumarin-chalcone compound may be 5 mM. In some embodiments, the coumarin-chalcone compound included in the composition may be the coumarin-chalcone compound C9.

In some embodiments, the effective amount of the coumarin-chalcone compound included in the composition may be used to reduce at least 10%, 20%, 30%, 40%, 50%, 60%, 70%, 80%, or 90% of the biofilm formed by *Pseudomonas aeruginosa, Escherichia coli, Staphylococcus aureus*, etc. The effective amount of the coumarin-chalcone compound included in the composition may be the coumarin-chalcone compound C9.

In some embodiments, when the composition is used to prevent, or disperse the biofilm or bacterial aggregate, a temperature may be in a range of 5° C. to 75° C. In some embodiments, the temperature may be in a range of 10° C. to 70° C. In some embodiments, the temperature may be in a range of 15 to 65° C. In some embodiments, the temperature may be in a range of 20° C. to 60° C. In some embodiments, the temperature may be in a range of 25° C. to 55° C. In some embodiments, the temperature may be in a range of 30° C. to 50° C. In some embodiments, the temperature may be in a range of 35° C. to 45° C. In some embodiments, the temperature may be in a range of 36° C. to 44° C. In some embodiments, the temperature may be in a range of 37° C. to 43° C. In some embodiments, the temperature may be in a range of 38° C. to 42° C. In some embodiments, the temperature may be in a range of 39° C. to 41° C.

In some embodiments, the composition containing the coumarin-chalcone compound may be contacted with the biofilm or bacterial aggregate. In some embodiments, the composition containing the coumarin-chalcone compound may be added to a growth medium of bacteria, for example, when it is necessary to monitor a growth state of the bacteria or measure a growth curve of the bacteria. The coumarin-chalcone compound included in the composition may be the coumarin-chalcone compound C9.

Exemplary techniques for determining a count of the bacteria may include an indirect culture counting technique and a direct counting technique. In some embodiments, the indirect culture counting technique may include a plate colony counting technique, a most probable number (MPN) technique (also known as a dilution culture count technique), etc. In some embodiments, the direct counting technique may include an optical microscope counting technique, a fluorescence microscope counting technique, a most probable number and polymerase chain reaction technique, a turbidity counting technique, an electrical impedance technique, a flow cytometer, or the like.

It should be noted that a plurality of types of vectors are known in the art. For example, plasmids and viral vectors such as retroviral vectors are known. Typically, factors of mammalian expression plasmids may include a starting point for replication, a suitable promoter, an optional enhancer, a necessary ribosomal binding site, a polyadenylation site, a splicing donor, a receptor site, a transcription termination sequence, and a 5' flanking non-transcription sequence. Exemplary vectors may include a plasmid (which may also be a carrier of another type of vector), an adenovirus, an adeno-associated virus (AAV), a lentivirus (e.g., modified HIV-1, SIV, or FIV), a retrovirus (e.g., ASV, ALV, or MoMLV), or a transposon (e. g., Sleeping Beauty, P-element, Tol-2, Frog Prince, piggyBac).

The present disclosure provides a method and a composition for inhibiting the formation of bacteria biofilm, the main advantages of which may include: the self-stable coumarin-chalcone compound may effectively inhibit the formation of the bacterial biofilm and reduce the virulence of the bacteria. In addition, the coumarin-chalcone compound combined with antibiotics may increase the susceptibility of the bacteria to antibiotics and reduce a minimal inhibitory concentration and a minimal biofilm eliminate concentration of antibiotics. The coumarin-chalcone compound may be expected to become a widely popular anti-biofilm agent.

The present disclosure may be described in detail below. The experimental methods in the following embodiments were conventional methods unless otherwise specified. The experimental materials and chemical reagents used in the following embodiments were purchased from biochemical reagent company unless otherwise specified. The quantitative experiments in the following embodiments were set to three repeated experiments, and each result was an average value.

Materials and Reagents

All solvents and chemicals reagent were used as purchased without further purification. Raw material 3-acetyl coumarin was purchased from Merck.

Luria-Bertani (LB) solid medium was prepared with 10 g tryptone, 5 g yeast extract, 10 g NaCl, 15 g agarose, and 1000 mL distilled water.

LB liquid medium was prepared with 10 g tryptone, 5 g yeast extract, 10 g NaCl, and 1000 mL distilled water.

Jensen liquid medium was prepared with 5 g NaCl, 2.51 g $K_2HPO_4$, 15.56 g L-glutamate monosodium, 2.81 g valine, 1.32 g phenylalanine, 13.87 g glucose, 0.165 g $MgSO_4.7H_2O$, 0.105 mg $CaCl_2.2H_2O$, 5.5 µg $FeSO_4.7H_2O$, 12 µg $ZnSO_4.7H_2O$, and 1000 mL distilled water.

Z-buffer was composed of 16.1 g/L $Na_2HPO_4.7H_2O$, 5.5 g/L $NaH_2PO_4.7H_2O$, 0.75 g/L KCl, 0.246 g/L, $MgSO_4.7H_2O$, whose pH is adjusted to 7.0, and then sterilized under 121° C. for 30 min.

Serum bottles with different oxygen partial pressures were prepared as follows. To prepare a serum bottle with 0.1% oxygen, first a serum bottle was filled with sterilized water. Two needles were inserted on the rubber stopper, one was connected to a drain pipe, the other is connected to an air inlet pipe. It should be noted that when plugging a rubber stopper on the serum bottle, a needle was inserted on the rubber stopper to eliminate air bubbles. After the water in the serum bottle was replaced with high-purity nitrogen (99.99% $N_2$), and ventilation and exhaust was continued for 3 min to balance the air pressure in the serum bottle with the atmospheric pressure. According to the oxygen concentration in the air of 20.8%, when the final oxygen concentration is 0.1%, 0.29 mL of air needs to be pumped. It should be understood that before pumping the air, an equal volume of nitrogen in the serum bottle was pumped out according to the calculated volume. Similarly, serum bottles with different oxygen partial pressures were prepared as described above.

TBST solution was prepared with 20 mM Tris, 137 mM NaCl, 0.1% tween 20, and pH of which was eventually adjusted to 7.6.

LBNS solid medium was prepared with 5 g yeast extract, 10 g tryptone, 15 g agar powder, and 1000 mL distilled water.

LBNS Liquid medium was prepared with 5 g yeast extract, 10 g tryptone and 1000 mL distilled water.

Swimming medium (or swimming plate) was composed of 10 g/L bacterial tryptone, 5 g/L yeast extract, and 1.5 g/L agar powder.

Twitching medium (or twitching plate) was composed of 10 g/L bacterial tryptone, 5 g/L yeast extract, and 1% agar powder.

Alkaline phosphatase buffer was prepared with 12.14 g Tris, 8 g NaCl, and 0.2033 g $MgCl_2 \cdot 6H_2O$, and pH of which was eventually adjusted to 9.0.

Bacterial Strains

*Pseudomonas aeruginosa* PAO1 is a wild-type *Pseudomonas aeruginosa* (see reference, Genetic Recombination In *Pseudomonas Aeruginosa*. J Gen Microbiol, 1955. 13: 572-581.).

WFPA800 is a mutant strain of *Pseudomonas aeruginosa* without the upstream promoter of pslA. WFPA800 was prepared by deleting a promoter of psl operon (see reference, Analysis of *Pseudomonas aeruginosa* conditional psl variants reveals roles for the Psl polysaccharide in adhesion and maintaining biofilm structure postattachment. *J Bacteriol*, 2006. 188: 8213-8221.).

WFPA801 is a mutant strain of *Pseudomonas aeruginosa* with Psl overexpression (see reference, Analysis of *Pseudomonas aeruginosa* conditional psl variants reveals roles for the Psl polysaccharide in adhesion and maintaining biofilm structure postattachment. *J Bacteriol*, 2006. 188: 8213-8221.).

pslA::lacZ is a mutant in which a β-galactosidase gene was inserted at a polysaccharide synthesis site of *Pseudomonas aeruginosa*. The primer sequence was SEQ ID NO: 1 (F: 5'-GGCCTGTTTCCCTACCT-3'); SEQ ID NO: 2 (R: 5'-GCGGATGTCGTGGTTG-3').

PAO1/pCdrA::gfp $(ASV)^C$ is a *Pseudomonas aeruginosa* mutant containing a plasmid that fuses the CdrA promoter with the gfp gene. The corresponding plasmid used to prepare pCdrA::gfp $(ASV)^C$ is pCdrA-gfp.

The contents of an ASCII text file titled "Sequence Listing", created on Feb. 15, 2022, and with a size of 1,433 bytes are hereby incorporated by reference.

Embodiment 1: Synthesis of Coumarin-Chalcone Compounds (C1-12)

The coumarin-chalcone compounds (C1-C12) were synthesized using a Claisen-Schmidt condensation reaction. The compound C9 may be taken as an example. The equivalent quantity of 3-acetyl coumarin (0.01 mol) and substituted benzaldehyde (0.01 mol) were taken in a 50 mL single neck round bottom flask, and 10 mL ethanol was added to the reaction mixture and stirred for 5 min. Then 2-3 drops of piperidine were added to the reaction mixture and the reaction mixture was reflux for 12 h to 15 h. The progress of the reaction was examined using thin layer chromatography (TLC). In the embodiment, the progress of all reactions was monitored on precoated silica gel plates (Merck, with fluorescent indicator UV254) using a hexane:ethyl acetate (70:30) system as a mobile phase, and spots were visualized by irradiation with ultraviolet light (254 nm). After the reaction was completed, the reaction mixture was quenched in crushed ice. The solid product was filtered, washed with water, and recrystallized from ethanol. The synthesis of other coumarin-chalcone derivatives (including C1-C8 and C10-C12) was consistent with the above method.

Embodiment 2: Biofilm Assay

1% inoculation amount of the bacterial solution cultured overnight was inoculated into 100 μL Jensen liquid medium. Different equal amounts of bacteria solution with C1 to C12, respectively, or without any additional substance were cultured in a 96-well polyvinyl chloride (PVC) plate (costar) overnight at 30° C. without agitation.

The bacterial biomass adsorbed on the 96-well PVC plate was detected by a crystal violet method, and steps were described as below. (1) The non-attached bacteria were removed using a pipettor, then the wells were gently rinsed with normal saline for 3 times. (2) A volume of 120 μL 0.1% crystal violet solution was added to stain the firmly attached bacterial cells in each well, which then staying static at room temperature for 30 min. (3) The PVC plate was taken out, the crystal violet solution was removed with a pipettor, and the non-attached crystal violet solution was washed with normal saline. (4) The crystal violet attached onto the PVC plate was dissolved with 200 μL of 30% acetic acid solution. The OD value of the acetic acid solution in each well was measured at 560 nm with a spectrophotometer.

In the embodiment, the effects of C1 to C12 on the biofilm were compared. As shown in FIG. 1, C9 reduced the contents of *Pseudomonas aeruginosa* PAO1 biofilm by 70%, C7 reduced the contents of *Pseudomonas aeruginosa* PAO1 biofilm by 60%, and C11 reduced the contents of *Pseudomonas aeruginosa* PAO1 biofilm by 55%. It can be seen from FIG. 1 that when a concentration of C9 was 5 mM, an inhibition rate may reach 70%, and the formation of *Pseudomonas aeruginosa* biofilm may be significantly inhibited when a concentration of C9 was in a range of 1 mM to 5 mM.

Embodiment 3: Growth Curve Analysis

*Pseudomonas aeruginosa* PAO1 (optical density $OD_{600} \approx 1.5$) was cultured in LB liquid medium overnight, and 1% inoculation amount of the bacterial solution was inoculated into a fresh LB liquid medium. Two equal amounts of bacterial solution with and without 5 mM coumarin-chalcone compound C9 were cultured in a shaking incubator with 200 rpm at 37° C. for 24 h. OD value of the bacterial solution at 600 nm was measured every hour with a spectrophotometer to trace bacterial growth.

Figure 2:
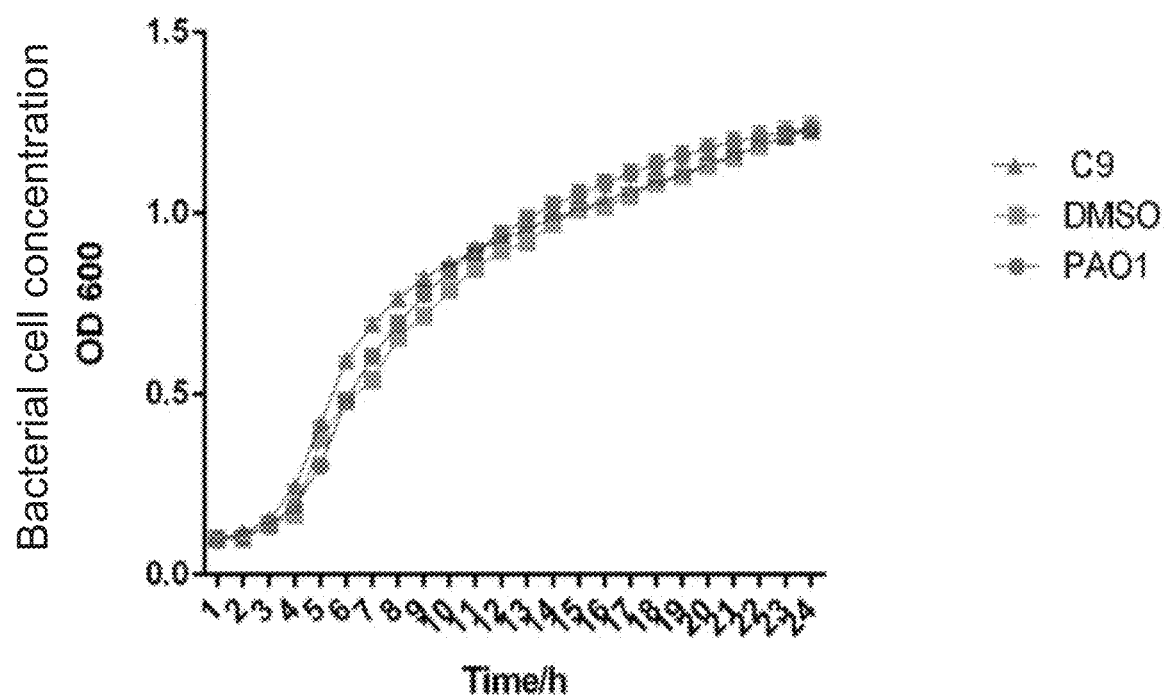
FIG. 2 illustrates bacterial growth curves of a blank group, a control group, and an experimental group treated with a coumarin-chalcone compound C9.

In the embodiment, the effect of the coumarin-chalcone compound C9 on $OD_{600}$ value of the bacterial solution was analyzed. As shown in FIG. 2, there was no significant difference in $OD_{600}$ value between the bacterial solution group with the coumarin-chalcone compound C9 and the control group. The embodiment illustrated that the coumarin-chalcone compound C9 has no significant effect on the growth of *Pseudomonas aeruginosa* PAO1.

Embodiment 4: Bacterial Motility Assay

PAO1 strains were inoculated into a LBNS agar plate and were cultured overnight at 37° C. Single colonies were respectively inoculated on the surface of swimming plates with and without the coumarin-chalcone compound C9, and cultured at 37° C. for 24 hours. Then, a diameter of a translucent area formed by bacterial swimming on each swimming plate was measured.

PAO1 strains were inoculated into a LBNS agar plate and were cultured overnight at 37° C. Single colonies were respectively stab-inoculated to the bottom of twitching plates with and without the coumarin-chalcone compound C9, and cultured at 37° C. for 24 hours. The growth of bacteria at an interface between the agar and the plastic plate was a twitching movement. When 1% TTC was added to the medium, the area that bacteria have visited may turn red, and then the diameter of the red area on each twitching plate was measured.

Figure 3:
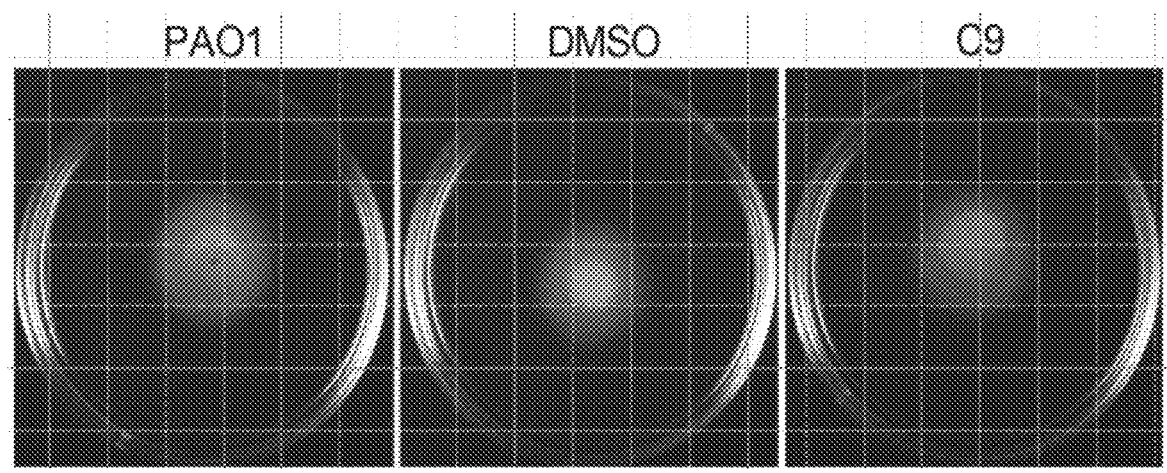
FIG. 3 is a schematic diagram illustrating effects on bacterial motility of a blank group, a control group, and an experimental group treated with a coumarin-chalcone compound C9.

In the embodiment, the performance of bacterial movement was analyzed. As shown in FIG. 3, the coumarin-chalcone compound C9 had no effect on the growth of *Pseudomonas aeruginosa*, the flagellate-mediated swimming ability, and the twitching motility mediated by type IV pili. Combined with FIG. 2, it has shown that the inhibition of the coumarin-chalcone compound C9 on biofilm was not due to any influence on the growth or the function of flagella or type IV pili.

Embodiment 5: Psl Immunoblot Analysis

*Pseudomonas aeruginosa* PAO1 was inoculated in Jensen media at 37° C. for 24 hours with shaking and treated with the coumarin-chalcone compound C9 (5 mM) or DMSO (5 mM), respectively. $OD_{600}$ values of the overnight cultured bacterial solutions were measured, and a bacterial solution with an OD (optical density) of 10 was collected. The bacterial solution with the OD of 10 was a bacterial solution whose $OD_{600}$ was 2 and the collected volume was 5 mL. The bacterial solution was centrifuged at 13000 r/min for 5 min and the corresponding supernatant was discarded. The obtained precipitate was dissolved in 100 µL of 0.5 M EDTA. Then the EDTA solution was boiled at 100° C. for 5 min and centrifuged, and the precipitate was discarded. The obtained supernatant was treated with proteinase K (final concentration, 0.5 mg/mL) for 1 h at 60° C., followed by inactivation of proteinase K for 30 min at 80° C. to obtain a polysaccharide extract. A volume of 3 µL of polysaccharide extract was spotted onto a nitrocellulose membrane and dried. After washing with TBST for 3 times, a blocking was done with 10% skimmed milk at room temperature for 1 h. The anti-Psl antibody (i.e., a primary antibody) (1:25,000 dilution) was added and then solution was treated at 25° C. for 1 h. After moistening with TBST for 3 times, the goat anti-rabbit IgG (i.e., secondary antibody) (1:10000 dilution) was added. After rinsing with alkaline phosphatase buffer, 5 mL of Western blue (Promega™) was added for staining. Western blot data was quantitatively analyzed using Image Lab™ 5.1 software.

In the embodiment, the effect of the coumarin-chalcone compound C9 on PSL production by *Pseudomonas aeruginosa* was analyzed. As shown in FIG. 4, the coumarin-chalcone compound C9 reduced 60% Psl production.

Embodiment 6: Activity Analysis of β-Galactosidase

1% inoculation amount of overnight cultured *Pseudomonas aeruginosa* (pslA::lacZ mutant strain) were respectively inoculated in Jensen media with and without coumarin-chalcone compounds C1-C12, and incubated at 37° C. until $OD_{600}$ reached to 0.5. Bacteria from 1.5 ml culture aliquots were resuspended in 200 µl Z-buffer and frozen/thawed three times to lyses bacteria. Cell lysates were assayed for both β-galactosidase activities as well as for total proteins by BCA assay (Pierce, USA). All β-galactosidase activity units were normalized by total protein per ml aliquot.

The units of β-galactosidase activity may be determined according to Equation (1) as follows:

$$\text{Miller units}=1000\times(OD_{420}-1.7\times OD_{550})/(t\times V\times OD_{600}) \quad (1)$$

where t denotes a time (unit: min), V denotes the volume (unit: mL).

Embodiment 7: Production of Psl Affected by pslA::lacZ Transcription Fusion

About 500 bp of DNA fragments upstream of ATG start codon of pslA gene were cloned into a polyclonal site of mini-CTX lacZ vector (note that the selected promoter fragment cannot affect the frameshift mutation). A recombinant plasmid (e.g., pTH2) was transferred into *Escherichia coli* S17-1λ pir. Then activated PAO1 was inoculated into 5 mL of LBNS medium, and S17-1/pTH2 strain was inoculated into 5 mL of LB medium with tetracycline (Tet) (12.5 µg/L), and both cultured overnight at 37° C. with 200 rpm. The overnight bacterial culture was centrifuged and resuspended into an antibiotic-free medium, with a ratio of $OD_{600}$ values of PAO1 to S17/pTH2 bacterial solution at about 1:2, to improve the conjugation efficiency. A volume of 7 µL PAO1 bacterial solution was spotted on an antibiotic-free LBNS plate and dried in a sterile workbench. Then 7 µL S17/pTH2 was dropped on the spot of PAO1, air-dried, and cultured overnight at 37° C. The overnight cultured bacterial sludge was placed on a LBNS plate containing Tet (100 µg/L) and Irg (25 µg/L), and then cultured at 37° C. until a single colony grows. Primer attb2/CTX1 (attB2: SEQ ID NO: 3 (GTCGCCGCCGGCGATGC), CTX1: SEQ ID NO: 4 (CCTCGTTCCCAGTTTGTTCC)) was used to verify whether the PCR product was correct. If the size of the PCR product was 950 bp, that is, the plasmid was integrated into the attB/P site of the chromosome of *Pseudomonas aeruginosa*. The resulting single colony was cultured overnight, and SM10/pFLP2 was cultured overnight. The two strains were conjugated by biparental mating operation as described above. The overnight cultured bacterial sludge was placed on a LBNS plate containing carb (300 µg/L) and Irg (25 µg/L), and then cultured at 37° C. until a single colony grows. A single colony was picked and streaked out on a 10% sucrose plate, and incubated at 30° C. until a single colony grows. Single colonies on the 10% sucrose plate were picked and spotted on the antibiotic-free LBNS plate and a LBNS plate containing carb (300 µg/L). The colonies that can grow on the antibody-free plate but cannot grow on the carb plate were selected for the next PCR verification. Primers AttB4/attB5 (attB4: SEQ ID NO: 5 (CGCCCTATAGTGAGTCG), attB5: SEQ ID NO: 6 (CGCCCCAACCTCGCTGG)) were used to PCR verification. If the size of the PCR product was 450 bp, the construction was correct. Thus, the strain containing the pslA promoter lacZ fusion was successfully constructed.

The results of pslA::lacZ transcription fusion further indicated that the coumarin-chalcone compound C9 affected the production of Psl at the transcription level, as shown in FIG. 5.

Embodiment 8: Analysis of Intracellular c-Di-GMP

The intracellular c-di-GMP may control the conversion of bacterial lifestyle between plankton and biofilm. In order to analyze an effect of the coumarin-chalcone compound C9 on a concentration of the intracellular c-di-GMP, direct and indirect methods were used to measure the level of c-di-GMP in *Pseudomonas aeruginosa*.

Since the transcription and expression of the extracellular protein CdrA was related to the intracellular concentration of cyclic diguanylic acid (c-di-GMP), PAO1/pCdrA::gfp$^s$ (ASV) was used to analyze c-di-GMP level indirectly.

FIG. 6 is a schematic diagram illustrating levels of intracellular c-di-GMP of a blank group, a control group, and an experimental group treated with a coumarin-chalcone compound C9, which are indicated by the green fluorescent intensity of pCdrA::gfp$^s$. As shown in FIG. 6, the embodiment indicated that the coumarin-chalcone compound C9 significantly reduced the fluorescence intensity of PAO1/pCdrA::gfp (ASV).

Figure 7:
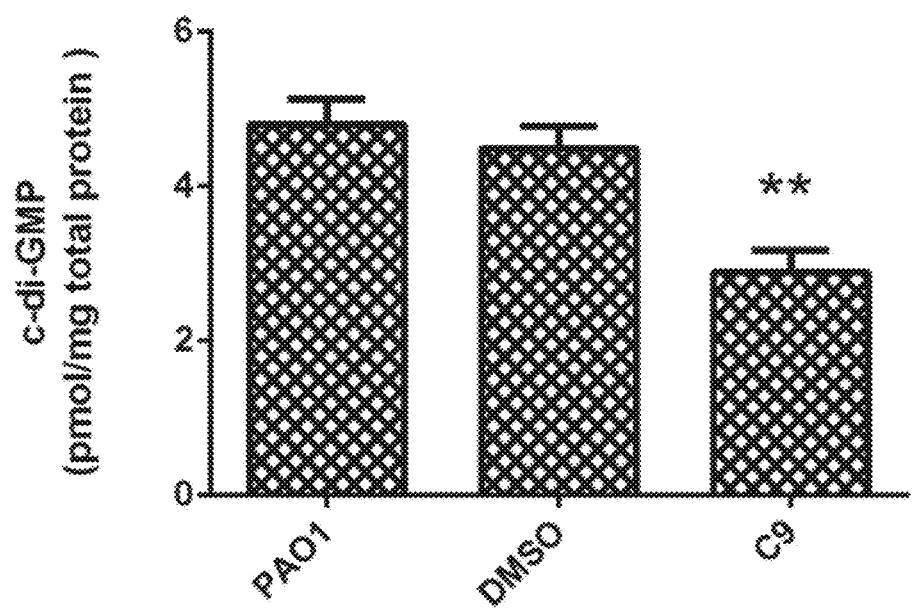
FIG. 7 is a schematic diagram illustrating LC-MS/MS-quantified intracellular c-di-GMP of a blank group, a control group, and an experimental group treated with a coumarin-chalcone compound C9.
Figure 8A:
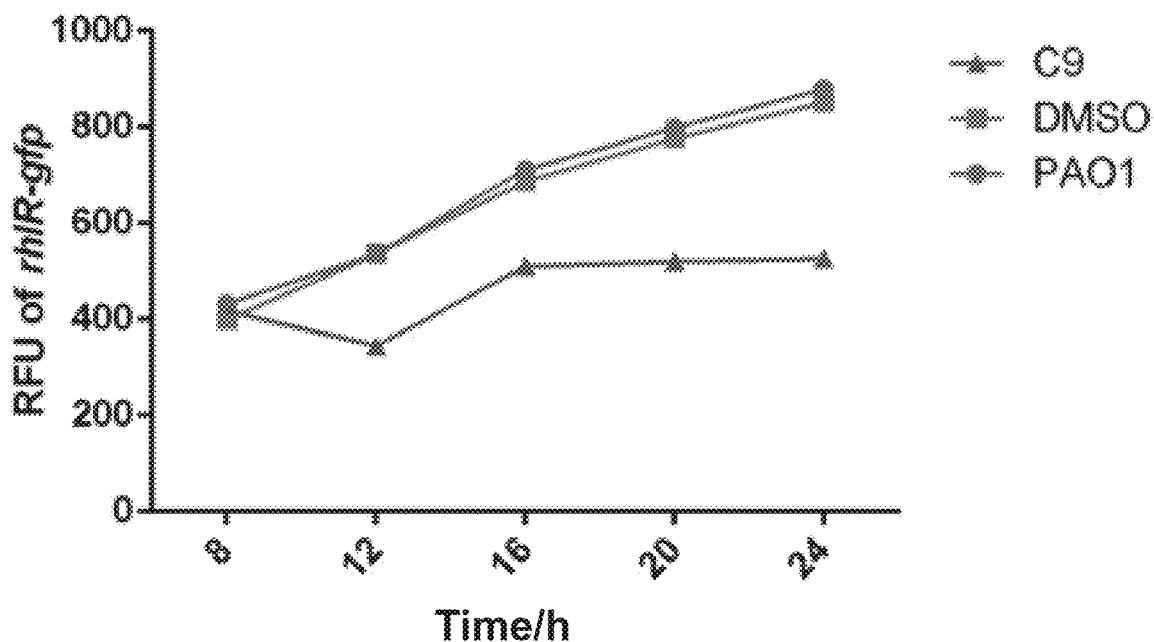
FIGS. 8A to 8D are schematic diagrams illustrating the inhibition of QS systems in *Pseudomonas aeruginosa* by compound C9.
Figure 8B:
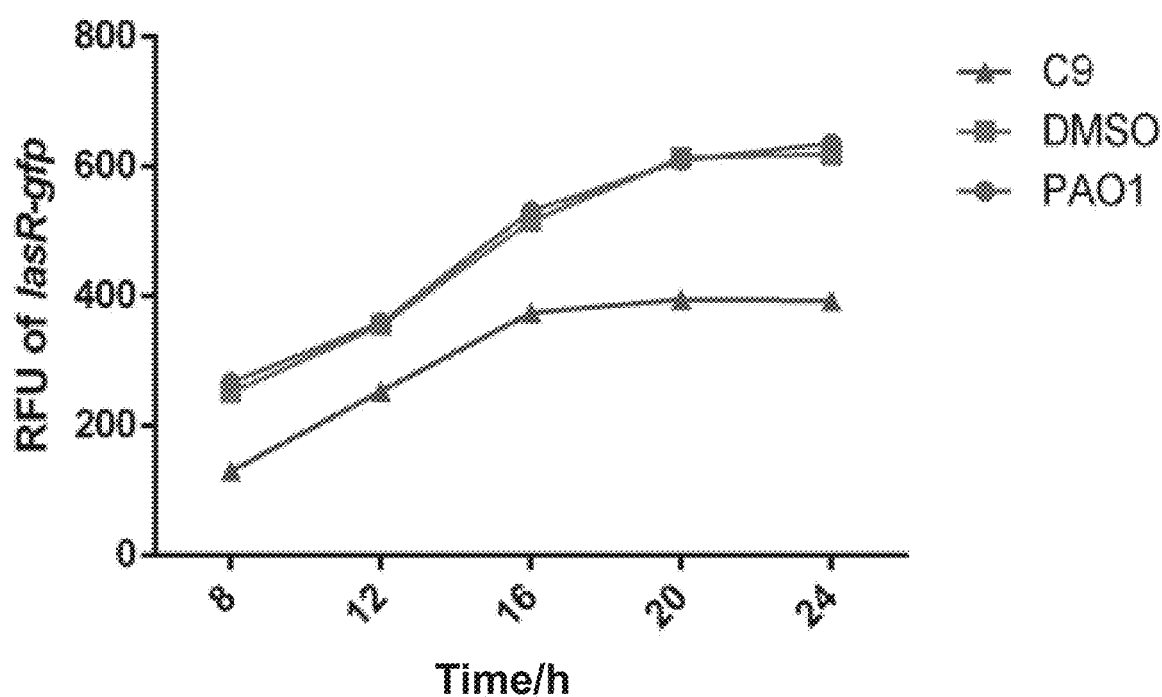
Figure 8C:
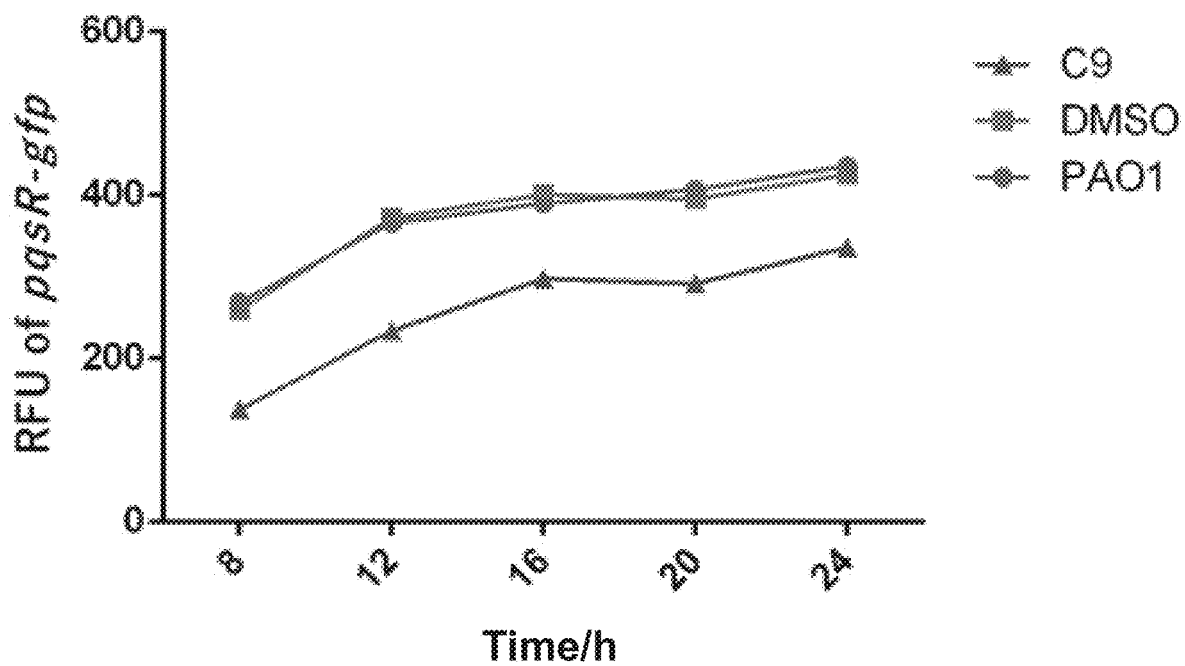
Figure 8D:
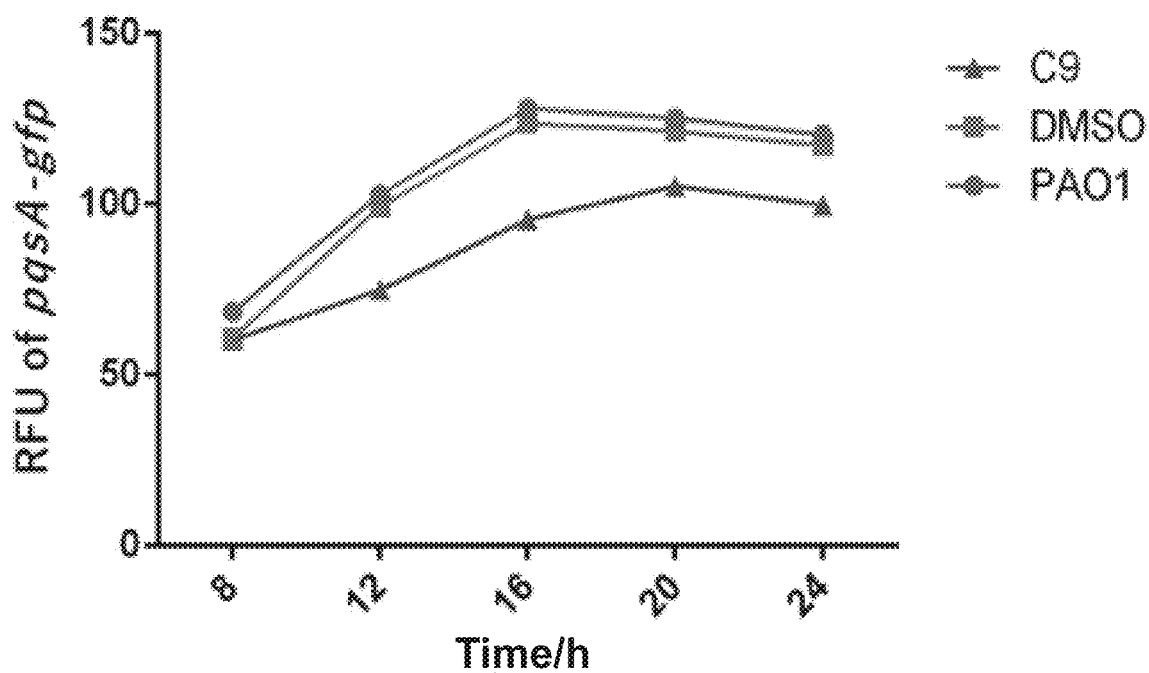

C-di-GMP was directly extracted from PAO1 strain grown with or without the coumarin-chalcone compound C9. The intracellular c-di-GMP was directly measured by LC-MS/MS quantification. As shown in FIG. 7, the coumarin-chalcone compound C9 treatment showed a 2-fold reduction on the c-di-GMP concentration, which was consistent with the results of the CdrA::gfp (ASV) gene reporter.

In the embodiment, the results indicated that the coumarin-chalcone compound C9 exposure can decrease an intracellular level of c-di-GMP in *Pseudomonas aeruginosa* PAO1.

Embodiment 9: Analysis of Gene Expression Level—the Coumarin-Chalcone Compound C9 Downregulated an Expression Level of QS Genes The QS system may regulate the formation of biofilm and the expression of multiple virulence factors. Whether the coumarin-chalcone compound C9 influences the QS regulation system was further studied. In the embodiment, a green fluorescent protein (GFP) was used as a reporter gene to examine the influence of the coumarin-chalcone compound C9 on the QS system. In this experiment, the transcription regulator genes (including LasR, RhIR, and PqsR) in three QS systems of *Pseudomonas aeruginosa* were used to study the gene expression of the QS system. By PCR expansion, promoter regions of the three genes were transcriptionally fused with a promoterless GFP fusion expression vector pProbe-AT, respectively, to construct transcription fusion plasmids that can indicate the expression level of LasR, RhIR, and PqsR genes, which were used as representatives of the expression of the three QS systems.

The overnight cultured bacterial solution was inoculated into the freshly prepared LB liquid medium to make its $OD_{600}$ at 0.25, and then cultured for 2 h. Fluorescence was measured at 4 h, 8 h, 12 h, 16 h, 20 h, 24 h, respectively, and the measurement was performed in a 96-well plate. Bacterial growth was monitored by measuring $OD_{600}$. The gene expression level was normalized by dividing the fluorescence value by the $OD_{600}$ value of each sample.

The effects of the coumarin-chalcone compound C9 on the transcription of the three known QS regulators LasR, RhIR, and PqsR were examined by gfp fusion. FIGS. 8A to 8D are schematic diagrams illustrating the inhibition of QS systems in *P. aeruginosa* by compound C9. The transcription of QS-related genes (LasI, LasR, RhII, RhIR, PqsA, and PqsR) was indicated by the green fluorescent intensity of GFP-tagged promoter region through pPROBE-AT' plasmid, the data of a blank group, a control group, and an experimental group treated with a coumarin-chalcone compound C9 were presented. As shown in FIGS. 8A to 8D, the coumarin-chalcone compound C9 downregulated the transcription of LasR, RhIR, and PqsR, respectively.

Molecular docking analysis may be used to understand how the coumarin-chalcone compound C9 interferes with QS regulation. The ligand docking results showed that the coumarin-chalcone compound C9 may strongly bind LasR and PqsR, and the coumarin-chalcone compound C9 exhibited weak binding to PqsA. The active compound scheme for docking was shown in Table (1).

TABLE 1 docking results: binding energy (kcal/mol) and hydrogen bond residues of the coumarin-chalcone compound C9 with LasR, PqsR, and PqsA

| Name | G-score | D-score | Lipophilic | H bond |
|---|---|---|---|---|
| LasR with C9 | −9.3 | −9.5 | −5.6 | −0.4 |
| PqsR with C9 | −9.2 | −9.2 | −5.6 | −0.4 |
| PqsA with C9 | −6.5 | −6.5 | −5.7 | −0.5 |

Embodiment 10: Reducing Virulence of *Pseudomonas aeruginosa*

The PAO1 culture inoculated with the coumarin-chalcone compound C9 (5 mM) was injected into a cabbage model and incubated at 37° C. for 36 hours. Then the colony phenotype was observed and colony-forming units (CFU) were calculated.

Figure 9:
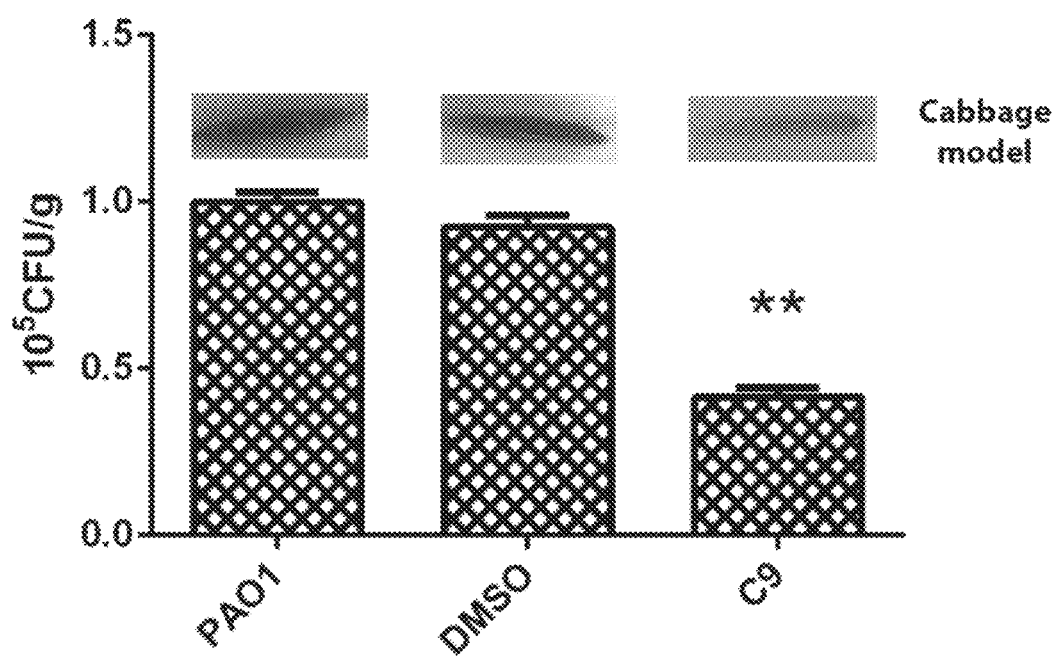
FIG. 9 is a schematic diagram illustrating virulences of bacteria of a blank group, a control group, and an experimental group treated with a coumarin-chalcone compound C9.

In the embodiment, the cabbage model was used to carry out the vivo experiment in vivo to study whether the coumarin-chalcone compound C9 affects the virulence of *Pseudomonas aeruginosa*. FIG. 9 is a schematic diagram illustrating virulences of bacteria of a blank group, a control group, and an experimental group treated with a coumarin-chalcone compound C9. As shown in FIG. 9, the results showed that the coumarin-chalcone compound C9 reduced the virulence of *Pseudomonas aeruginosa* in the cabbage model by 60%. This result was consistent with the effect of the coumarin-chalcone compound C9 on QS regulation.

Embodiment 11: Stability of the Coumarin-Chalcone Compound C9 and its Potential as an Anti-Biofilm Drug Physicochemical properties of a compound (e.g., permeability and lipophilicity of a biofilm) may be significantly affected by pKa values of the compound. Since a variable range of human pH includes both acidity and alkalinity, whether the compound is stable in different pH ranges may be very important.

UV-Vis spectral analysis was used to study the stability of the coumarin-chalcone compound C9 at a pH range of 3.4 to 8.4. It was found that an initial pH of the coumarin-chalcone compound C9 was 6.9 and gradually reduced to about pH=2 by slow titration with HCl (25 mM). After reaching pH=2, KOH (25 mM) was added slowly until the pH reached 12. In this way, a graph of a relationship between the pH and the volume of KOH added was plotted to find an equivalent point and thus the pKa.

Figure 10A:
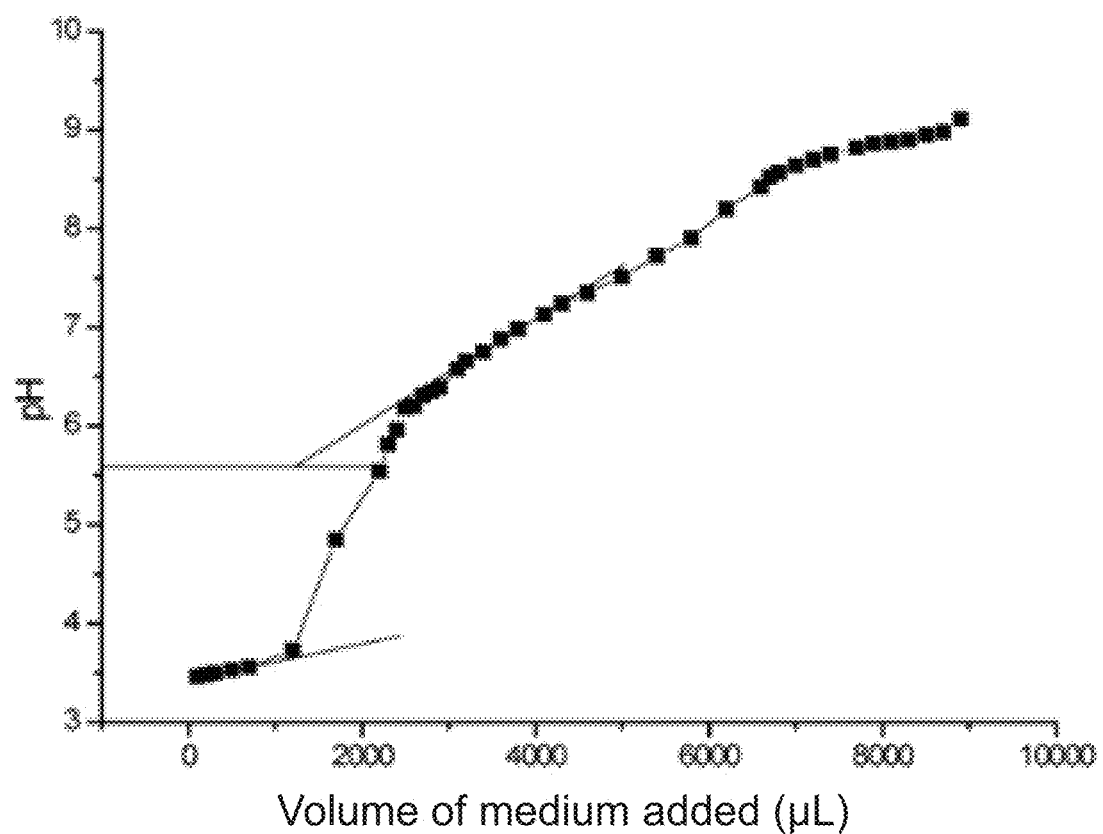
FIGS. 10A to 10C are schematic diagrams illustrating a stability of a coumarin-chalcone compound C9.
Figure 10B:
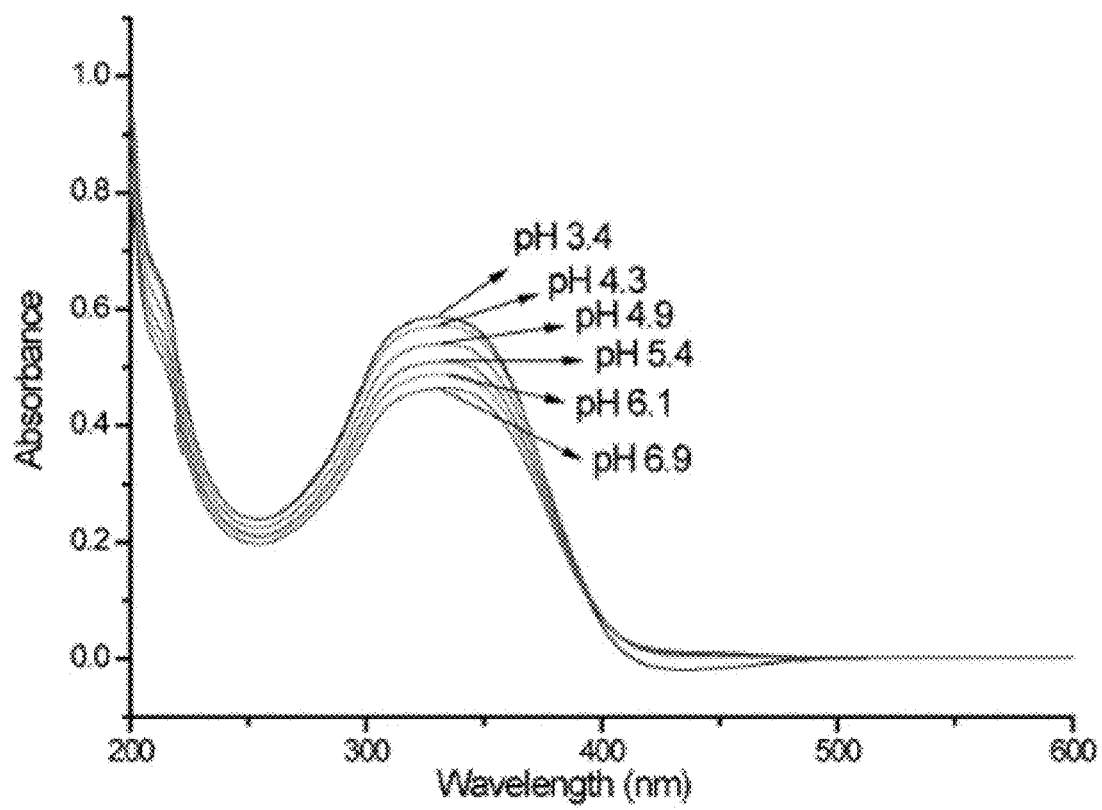
Figure 10C:
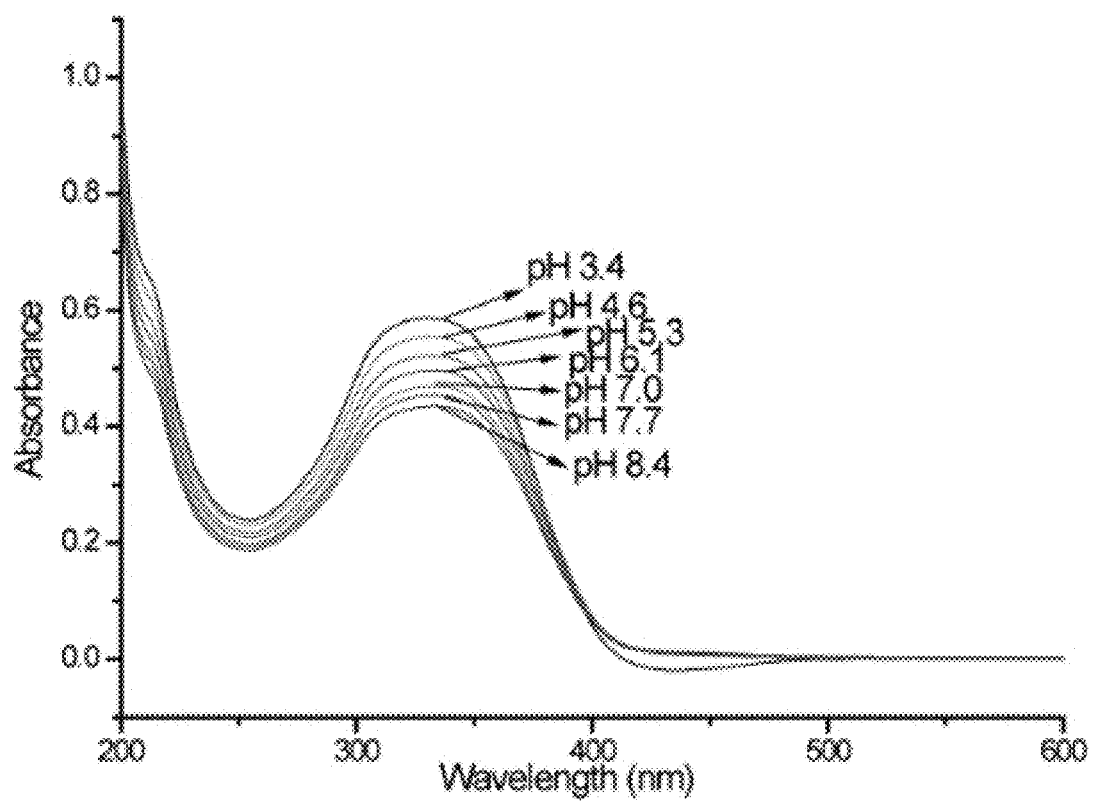

In the embodiment, the stability of the coumarin-chalcone compound C9 was studied. FIGS. 10A to 10C are schematic diagrams illustrating the stability of a coumarin-chalcone compound C9. As shown in FIGS. 10A to 10C, the pKa value of the active coumarin-chalcone compound C9 was found to be 5.66, indicating that the compound may have an ability to be absorbed through a lipid membrane barrier and may also enter target cells to act. The UV absorption spectroscopy in the pH range of 3.4 to 8.4 further supported the stability of the coumarin-chalcone compound C9. First, HCl (25 mM) was continually added to the coumarin-chalcone compound C9 (initial pH=6.9) until the pH reached 3.4 (FIG. 10B), resulting in an increase in the strength of an absorption band at 330 nm. Subsequently, the pH was gradually reduced from 3.4 to 8.4 by titration with KOH (25 mM) (FIG. 10C). The reversibility of the reaction indicated that protonation occurred during the titration with HCl. It was also clear that the absorption band maintained its position throughout the experiment, no additional bands were detected, and the original absorption band remained intact, which illustrated that the coumarin-chalcone compound C9 was stable at different pH conditions. The stability of the coumarin-chalcone compound C9 indicated a great potential to be an anti-QS and anti-biofilm drug.

Figure 11:
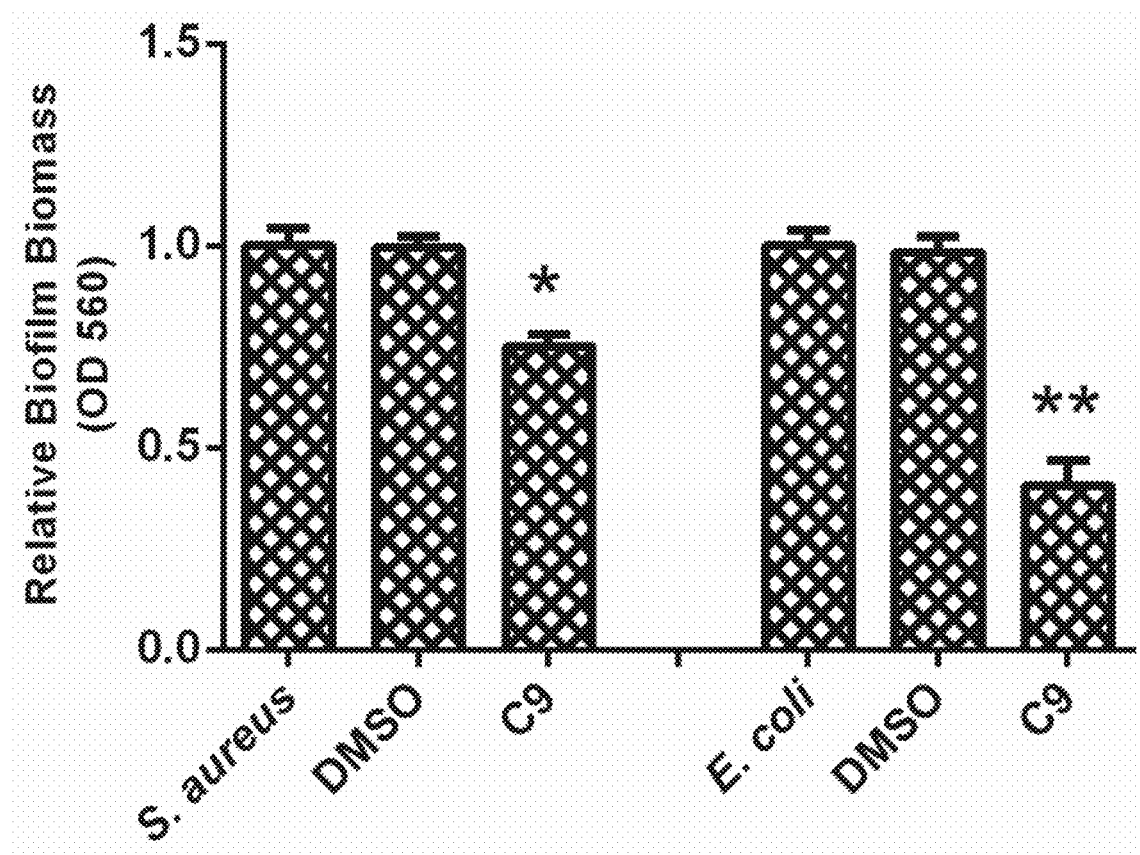
FIG. 11 is a schematic diagram illustrating an inhibiting effect of a coumarin-chalcone compound C9 on *Staphylococcus aureus* and *Escherichia coli* biofilms.

Embodiment 12: Effects of the Coumarin-Chalcone Compound C9 on Other Biofilms of Bacteria FIG. 11 is a schematic diagram illustrating an inhibiting effect of a coumarin-chalcone compound C9 on *Staphylococcus aureus* and *Escherichia coli* biofilms. As shown in FIG. 11, the coumarin-chalcone compound C9 showed an inhibitory effect on a biofilm of Gram positive pathogens (e.g., *Staphylococcus aureus*) or Gram negative bacteria (e.g., *Escherichia coli*) using the above 96-well plate crystal violet biofilm detection method. Compared with *Staphylococcus aureus* biofilm (30% reduction), the coumarin-chalcone compound C9 had better activity against *Escherichia coli* biofilm (about 60% reduction).

Embodiment 13: Effect of the Coumarin-Chalcone Compound C9 in Combination with Antibiotic In the experiment, the coumarin-chalcone compound C9 (5 mM) was added to a culture medium, and an inhibition area of the corresponding antibiotics was measured by a conventional filter paper method. As shown in FIG. 12, the susceptibility of *Pseudomonas aeruginosa* (right image) treated with the coumarin-chalcone compound C9 to fluoroquinolone antibiotics (CIP) was significantly higher than that of the control group (left image), indicating that the coumarin-chalcone compound C9 may enhance the susceptibility of bacteria to antibiotics through some unknown way or mechanism and may have the potential to decrease antibiotic resistance.

Embodiment 14: The Coumarin-Chalcone Compound C9 May Decrease a Minimal Inhibitory Concentration (MIC) and a Minimal Biofilm Eliminate Concentration (MBEC) with Respect to *Pseudomonas aeruginosa*

MIC and MBEC values of a biofilm formed on a peg of a calgary biofilm device (CGM and CBD) treated with the coumarin-chalcone compound C9 were measured according to methods (Innovotech) in MBEC™ high throughput experimental operation manual. Biofilm treated with the coumarin-chalcone compound C9 (5 mM) was cultured in an antibiotic-containing medium in a 96-well plate for 24 h, and the MIC value was obtained by measuring the $OD_{600}$ of planktonic cells of the above samples. To determine the MBEC value, the biofilm treated with the coumarin-chalcone compound C9 (5 mM) was cultured in an antibiotic-containing medium in a 96-well plate for 24 h, then the biofilm was ultrasonically crushed and subsequently incubated at 37° C. for another 24 hours. Biomass of newly formed biofilms was recorded to indicate the corresponding MBEC value.

Figure 13A:
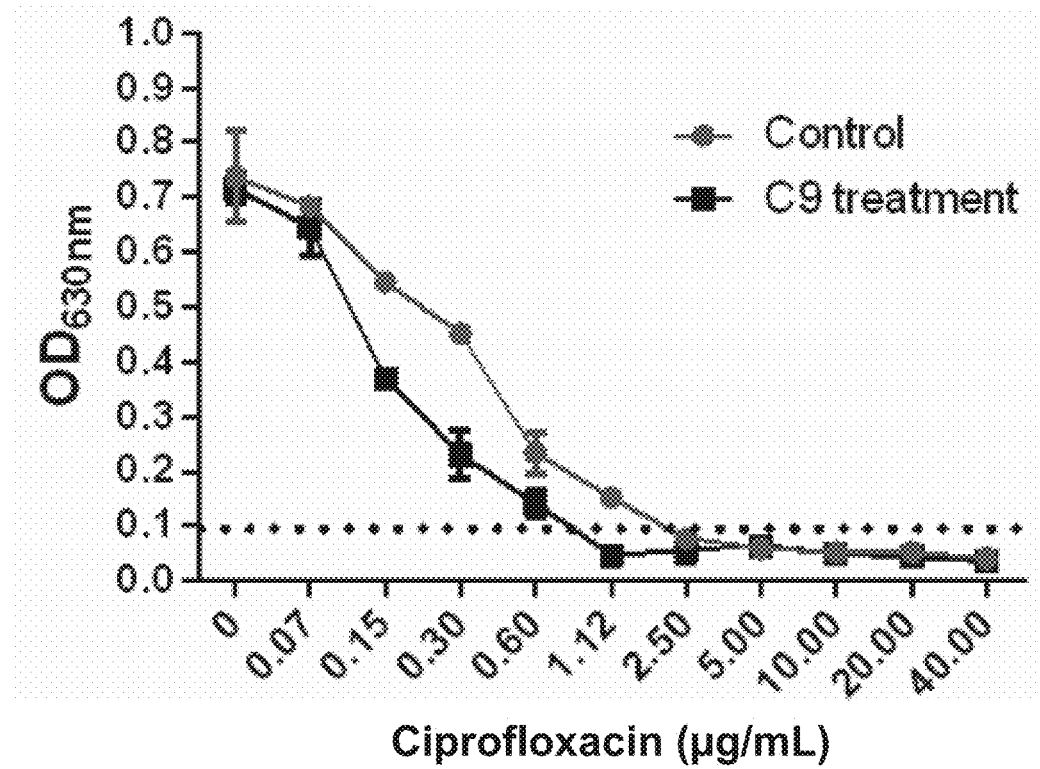
FIGS. 13A to 13B are schematic diagrams illustrating an effect of a coumarin-chalcone compound C9 on reducing a minimal inhibitory concentration of bacteria biofilm to a drug.
Figure 13B:
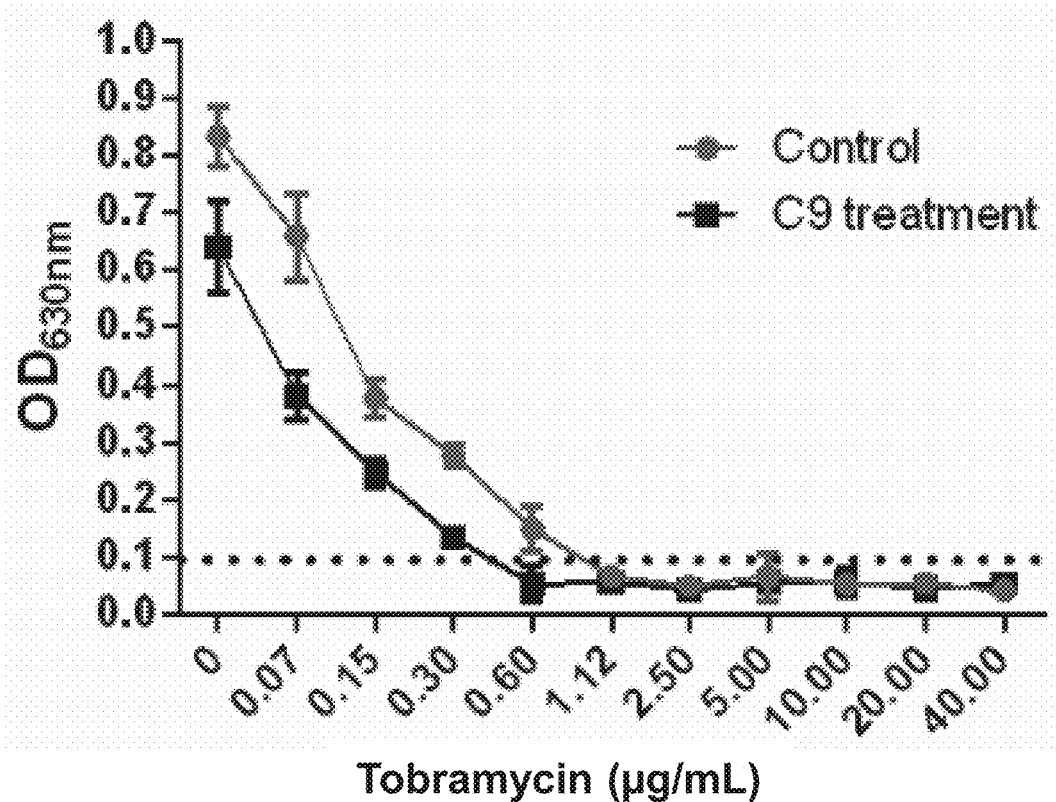
Figure 14A:
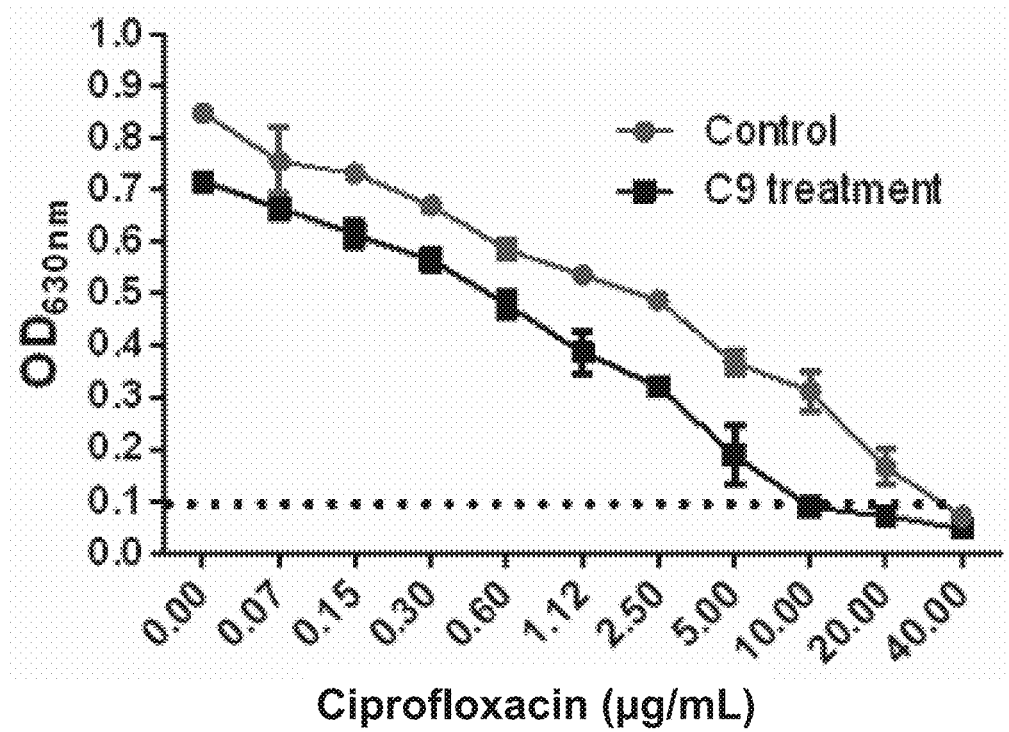
FIGS. 14A to 14B are schematic diagrams illustrating an effect of a coumarin-chalcone compound C9 on reducing a minimal biofilm eliminate concentration of bacteria biofilm to a drug.
Figure 14B:
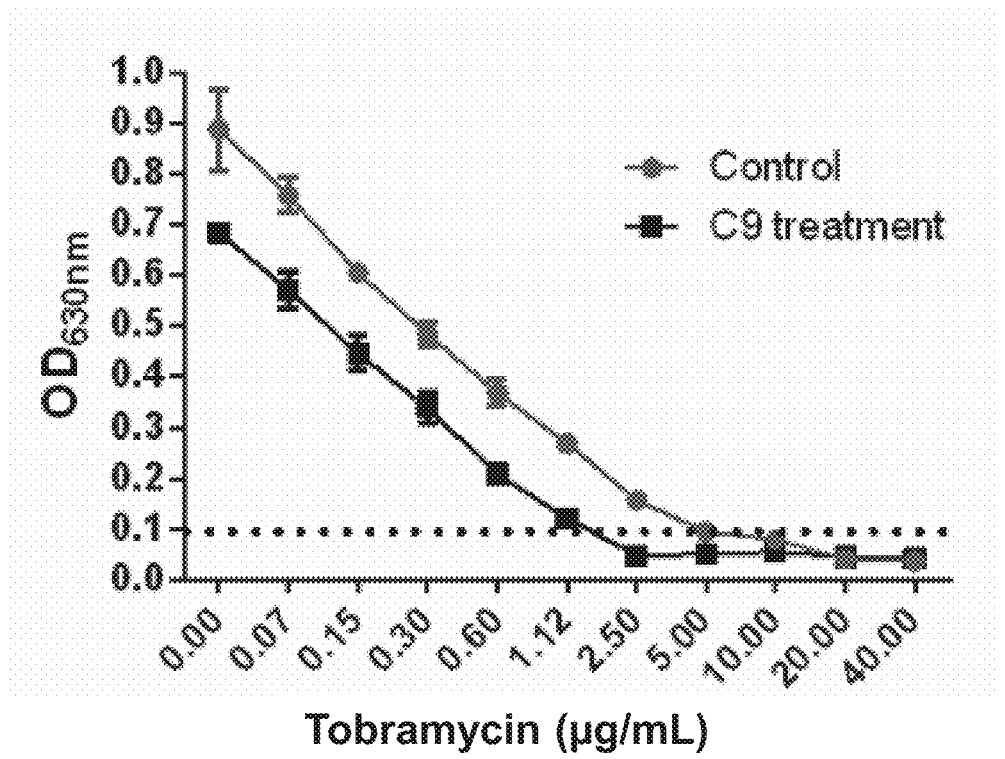

FIGS. 13A to 13B are schematic diagrams illustrating an effect of a coumarin-chalcone compound C9 on reducing a minimal inhibitory concentration of bacteria biofilm to a drug. FIGS. 14A to 14B are schematic diagrams illustrating an effect of a coumarin-chalcone compound C9 on reducing a minimal biofilm eliminate concentration of bacteria biofilm to a drug. As shown in FIGS. 13A to 13B, and FIGS. 14A to 14B, after being treated with the coumarin-chalcone compound C9, the MBEC and MIC of a biofilm against either ciprofloxacin or tobramycin was significantly lower than those in untreated group.

The basic concepts have been described. Obviously, for those skilled in the art, the detailed disclosure may be only an example and does not constitute a limitation to the present disclosure. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

In some embodiments, the numbers expressing quantities of ingredients, properties, and so forth, used to describe and claim certain embodiments of the application are to be understood as being modified in some instances by the term "about," "approximate," or "substantially". Unless otherwise stated, "about," "approximate," or "substantially" may indicate ±20% variation of the value it describes. Accordingly, in some embodiments, the numerical parameters set forth in the description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable.

Each patent, patent application, patent application publication and other materials cited herein, such as articles, books, instructions, publications, documents, etc., are hereby incorporated by reference in their entirety. Application history documents that are inconsistent or conflicting with the contents of the present disclosure are excluded, and documents (currently or later attached to the present disclosure) that limit the widest range of the scope of the present disclosure are also excluded. It should be noted that if the description, definition, and/or terms used in the appended application of the present disclosure is inconsistent or conflicting with the content described in the present disclosure, the use of the description, definition and/or terms of the present disclosure shall prevail.

At last, it should be understood that the embodiments described in the present disclosure are merely illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A method for inhibiting formation of a biofilm of bacteria, comprising:
treating the bacteria with an effective amount of a coumarin-chalcone compound, wherein a molecular formula of the coumarin-chalcone compound is

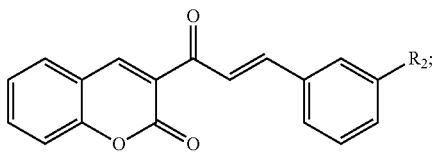

wherein $R_2$ is selected from —$OCH_3$, —Cl, —Br, —$NO_2$.

2. The method of claim 1, wherein the coumarin-chalcone compound inhibits the formation of the biofilm by reducing production of Psl polysaccharide in the bacteria at a transcription level.

3. The method of claim 1, wherein the coumarin-chalcone compound inhibits the formation of the biofilm by reducing a level of c-di-GMP in the bacteria, and the c-di-GMP is able to promote conversion of plankton into the biofilm.

4. The method of claim 1, wherein the coumarin-chalcone compound inhibits the formation of the biofilm by reducing quorum sensing, virulence factors regulated by the quorum sensing is reduced by downregulating the expression of quorum sensing regulators in the bacteria, and the quorum sensing regulators include at least one of LasR, RhlR, or PqsR.

5. The method of claims 1, wherein a concentration of the effective amount of the coumarin-chalcone compound is 5 mM.

6. The method of claim 1, wherein the effective amount of the coumarin-chalcone compound inhibits the formation of at least 30% of the biofilm when other conditions are the same.

7. The method of claim 1, wherein the effective amount of the coumarin-chalcone compound further reduces virulence of the bacteria.

8. The method of claim 1, wherein the bacteria include Gram negative bacteria.

9. The method of claim 8, wherein the Gram negative bacteria include *Pseudomonas aeruginosa* or *Escherichia coli*.

10. The method of claim 1, wherein the bacteria include Gram positive bacteria.

11. The method of claim 10, wherein the Gram positive bacteria include *Staphylococcus aureus*.

12. The method of claim 1, wherein the effective amount of the coumarin-chalcone compound inhibits the formation of at least 50% of the biofilm when other conditions are the same.

13. The method of claim 1, wherein the effective amount of the coumarin-chalcone compound inhibits the formation of at least 60% of the biofilm when other conditions are the same.

14. The method of claim 1, wherein the bacteria are *Staphylococcus aureus*, and the effective amount of the coumarin-chalcone compound inhibits the formation of at least 30% of *Staphylococcus aureus* biofilm when other conditions are the same.

15. The method of claim 1, wherein the bacteria are *Escherichia coli*, and the effective amount of the coumarin-chalcone compound inhibits the formation of at least 60% of *Escherichia coli* biofilm when other conditions are the same.

16. The method of claim 1, wherein the bacteria are *Pseudomonas aeruginosa*, and the effective amount of the coumarin-chalcone inhibits the formation of at least 70% of *Pseudomonas aeruginosa* biofilm when other conditions are the same.

17. The method of claim 1, wherein the molecular formula of the coumarin-chalcone compound is

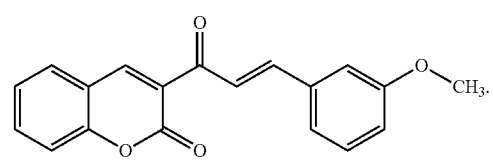 [SMILES: COc1cccc(/C=C/C(=O)c2cc3ccccc3oc2=O)c1]

18. A composition for inhibiting formation of a biofilm, comprising an effective amount of a coumarin-chalcone compound, wherein a molecular formula of the coumarin-chalcone compound is

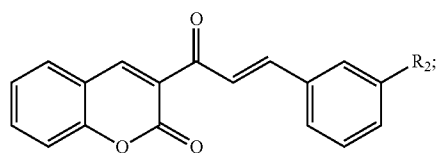

wherein $R_2$ is selected from —$OCH_3$, —Cl, —Br, —$NO_2$;

wherein the composition further comprises an antibiotic including at least one of amoxicillin, doxycycline, tetracycline, minocycline, cephalexin, cefuroxime, ciprofloxacin, moxifloxacin, clindamycin, lincomycin, clarithromycin, azithromycin, sulfapyridine, sulfamoxole, dalbavancin, telavancin , gentamicin, tobramycin, meropenem, doripenem, metronidazole, or levofloxacin.

19. The composition of claim 18, wherein the composition is configured to reduce production of Psl polysaccharide at a transcription level.

20. The composition of claim 18, wherein the composition is further configured to reduce a minimal inhibitory concentration of the antibiotic and a minimal biofilm eliminate concentration of the antibiotic.

* * * * *

SEQUENCE LISTING

```
<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Synthetic sequence

<400> SEQUENCE: 1
ggcctgtttc cctacct                                                  17

<210> SEQ ID NO 2
<211> LENGTH: 16
<212> TYPE: DNA
<213> ORGANISM: Artificial Sequence
<220> FEATURE:
<223> OTHER INFORMATION: Synthetic sequence

<400> SEQUENCE: 2
gcggatgtcg tggttg                                                   16

<210> SEQ ID NO 3
<211> LENGTH: 17
<212> TYPE: DNA
<213> ORGANISM: Artificial Sequence
<220> FEATURE:
<223> OTHER INFORMATION: Synthetic sequence

<400> SEQUENCE: 3
gtcgccgccg gcgatgc                                                  17

<210> SEQ ID NO 4
<211> LENGTH: 20
<212> TYPE: DNA
<213> ORGANISM: Artificial Sequence
<220> FEATURE:
<223> OTHER INFORMATION: Synthetic sequence

<400> SEQUENCE: 4
cctcgttccc agtttgttcc                                               20

<210> SEQ ID NO 5
<211> LENGTH: 17
<212> TYPE: DNA
<213> ORGANISM: Artificial Sequence
<220> FEATURE:
<223> OTHER INFORMATION: Synthetic sequence

<400> SEQUENCE: 5
cgccctatag tgagtcg                                                  17

<210> SEQ ID NO 6
<211> LENGTH: 17
<212> TYPE: DNA
<213> ORGANISM: Artificial Sequence
<220> FEATURE:
<223> OTHER INFORMATION: Synthetic sequence

<400> SEQUENCE: 6
cgccccaacc tcgctgg                                                  17
```